(12) United States Patent
Becker et al.

(10) Patent No.: US 9,637,745 B2
(45) Date of Patent: *May 2, 2017

(54) IMPAIRED WOUND HEALING COMPOSITIONS AND TREATMENTS

(71) Applicant: CoDa Therapeutics, Inc., San Diego, CA (US)

(72) Inventors: David Lawrence Becker, Hertfordshire (GB); Colin Richard Green, Epson (NZ); Bradford James Duft, San Diego, CA (US)

(73) Assignee: CoDa Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/709,382

(22) Filed: May 11, 2015

(65) Prior Publication Data

US 2015/0315598 A1 Nov. 5, 2015

Related U.S. Application Data

(63) Continuation of application No. 13/764,674, filed on Feb. 11, 2013, now Pat. No. 9,029,339, which is a continuation of application No. 13/295,020, filed on Nov. 11, 2011, now Pat. No. 8,685,940, which is a continuation of application No. 12/001,498, filed on Dec. 11, 2007, now Pat. No. 8,063,023.

(60) Provisional application No. 60/874,404, filed on Dec. 11, 2006.

(51) Int. Cl.

| A61K 31/70 | (2006.01) |
|---|---|
| C07H 21/02 | (2006.01) |
| C07H 21/04 | (2006.01) |
| C12N 15/113 | (2010.01) |
| A61K 31/7105 | (2006.01) |
| C12Q 1/68 | (2006.01) |

(52) U.S. Cl.
CPC ...... *C12N 15/1138* (2013.01); *A61K 31/7105* (2013.01); *C12N 2310/11* (2013.01)

(58) Field of Classification Search
None
See application file for complete search history.

(56) References Cited

U.S. PATENT DOCUMENTS

| 5,044,810 A | 9/1991 | Matsuoka et al. |
|---|---|---|
| 5,166,195 A | 11/1992 | Ecker |
| 7,098,190 B1 | 8/2006 | Becker et al. |
| 7,153,822 B2 | 12/2006 | Jensen et al. |
| 7,250,397 B2 | 7/2007 | Larsen et al. |
| 7,919,474 B2 | 4/2011 | Green et al. |
| 2004/0092429 A1 | 5/2004 | Jensen et al. |
| 2005/0119211 A1 | 6/2005 | Chowrira et al. |

FOREIGN PATENT DOCUMENTS

| JP | 2002-535377 A | 10/2002 |
|---|---|---|
| WO | WO-96-19194 | 6/1996 |
| WO | WO-98-24797 | 6/1998 |
| WO | WO-00-44409 | 8/2000 |
| WO | WO-03-032964 | 4/2003 |
| WO | WO-03-063891 | 8/2003 |
| WO | WO-2005-053600 | 6/2005 |
| WO | WO-2005-119211 | 12/2005 |
| WO | WO-2006-069181 | 6/2006 |
| WO | WO-2006-134494 | 12/2006 |
| WO | WO-2008-060622 | 5/2008 |
| WO | WO-2008-073479 | 6/2008 |
| WO | WO-2008-151022 | 12/2008 |
| WO | WO-2009-075881 | 6/2009 |
| WO | WO-2009-075882 | 6/2009 |

OTHER PUBLICATIONS

Abdulla et al., "Cell-to-Cell Communication and Expression of Gap Junctional Proteins in Human Diabetic and Nondiabetic Skin Fibroblasts," *Endocrine*, 1999, 10(1):35-41.
Agrawal, "Antisense oligonucleotides; towards clinical trials," *TIBTECH*, 1996, 14:376-387.
Altschul, "Basic Local Alignment Search Tool," *Journal of Molecular Biology*, 1990, 215:403-410.
Altschul, "A Protein Alignment Scoring System Sensitive at All Evolutionary Distances," *Journal of Molecular Evolution*, 1993, 36:290-300.
Baldwin et. al., "Growth factors in corneal wound healing following refractive surgery: A Review," *ACTA Ophthalmologica Scandinavica*, 2002, 80(3):238-247.
BBC News, "Gels 'heal wounds more quickly,'" May 26, 2006, accessed online at http://news.bbc.co.uk/1/hi/health/3243633.stm, 2 pages.
Becker et al., "Gap junction-mediated interactions between cells," *Cell-Cell Interactions—A Practical Approach*, Chapter 3, Fleming, ed., 2001, Oxford University Press, pp. 47-70.
Becker et al., "Role of gap junctions in the development of the preimplantation mouse embryo," *Microsc. Res. Tech*, 1995, 31:364-374.
Becker et al., "Connexin α1 and cell proliferation in the developing chick retina." *Experimental Neurology*, Apr. 1999, 156(2):326-332.
Becker et al., "Roles for α1 connexin in morphogenesis of chick embryos revealed using a novel antisense approach," *Development Genetics*, 1999, 24:33-42.
Becker et al., "Cell coupling in the retina: Patterns and purpose," *Cell Biology International*, 1988, 22(11-12):781-792.
Becker et al., "Changing patterns of ganglion cell coupling and connexin expression during chick retinal development," *J. Neurobiol.*, 2002, 52:280-293.
Becker et al., "Use of pIRES vectors to express EGFP and connexin constructs in studies of the role of gap junctional communication in the early development of the chick retina and brain," *Cell Communication and Adhesion*, 2001, 8(4-6):355-359.
Becker et al., "Expression of major gap junction connexin types in the working myocardium: Mammals are not typical vertebrates," *Cell Biology International*, 1998, 22(7-8):527-543.
Becker et al., "The relationship of gap junctions and compaction in the preimplantation mouse embryo," *Development*, 1992 Supplement:113-118.
Becker et al., Functional analysis of amino acid sequences in connexin 43 involved in intercellular communication through gap junctions, *Journal of Cell Science*, 1995, 108:1455-1467.
Becker et al., "Functional block of gap junctional communication using antipeptide antibodies: Molecular localization of the putative binding sites," *Progress in Cell Research*, 1995, 4:427-430.

(Continued)

*Primary Examiner* — Sean McGarry
(74) *Attorney, Agent, or Firm* — Duane Morris LLP

(57) ABSTRACT

Connexin modulation for the treatment of wounds that do not heal at expected rates, including delayed healing wounds, incompletely healing wounds, and chronic wounds, and associated methods, compositions and articles.

22 Claims, 4 Drawing Sheets

(56) References Cited

OTHER PUBLICATIONS

Becker et al., "Pluronic gel as a means of antisense delivery," *Antisense Techniques in the CNS: A Practical Approach*, Leslie et al., eds., 1999, Oxford University Press, pp. 149-157.

Bennett et al., "Electrical coupling and neuronal synchronization in the Mammalian brain," *Neuron*, Feb. 19, 2004, 41:495-511.

Berkovitz et al., "The detailed morphology and distribution of gap junction protein associated with cells from the intra-articular disc of the rat temporomandibular joint," *Connective Tissue Research*, 2003, 44:12-18.

Berthoud et al. "Peptide inhibitors of intercellular communication," *Am J. Physiol Lung Cell Mol. Physiol.*, 2000, 279:L619-L622.

"Biology of Reproduction: Official Journal of the Society for the Study of Reproduction," Database Biosis Biosciences Information Service, Jun. 12, 1998, Philadelphia, 58(6):78.

Bittman et al., "Connexin expression in homotypic and heterotypic cell coupling in the developing cerebral cortex," *The Journal of Comparative Neurology*, 2002, 443:201-212.

Blackburn et al., "Connexin43 gap junction levels during development of the thoracic aorta are temporally correlated with elastic laminae deposition and increased blood pressure," *Cell Biology International*, Feb. 21, 1997, PMID: 9080656 [PubMed—indexed for MEDLINE], 21(2):87-97.

Blackburn et al., "Upregulation of connexin43 gap junctions during early stages of human coronary atherosclerosis," *Arteriosclerosis, Thrombosis, and Vascular Biology*, Aug. 15, 1995, PMID: 7627716 [PubMed—indexed for Medline], 8:1219-1228.

Boitano et al., "Connexin mimetic peptides reversibly inhibit $Ca^{2+}$ signaling through gap junctions in airway cells," *Am. J. Physiol. Lung Cell Mol. Physiol.*, 2000, 279:L623-L630.

Brandner et al., "Connexins 26, 30, and 43: Differences Among Spontaneous, Chronic, and Accelerated Human Wound Healing," *The Journal of Investigative Dermatology*, May 5, 2004, 122:1310-1320.

Braet et al., "Pharmacological sensitivity of ATP release triggered by photoliberation of inositol-1,4,5-trisphosphate and zero extracellular calcium in brain endothelial cells," *Journal of Cellular Physiology*, 2003, 197(2):205-213.

Branch, "A good antisense molecule is hard to find," *TIBS*, Feb. 1998, 23:45-50.

Brummelkamp et al., "A System for Stable Expression of Short Interfering RNAs in Mammalian Cells," *Science*, Apr. 19, 2002, 296:550-553.

Camelliti et al., "Spatially and temporally distinct expression of fibroblast connexins after sheep ventricular infarction," *Cardiovascular Research*, 2004, PMID: 15094361 [PubMed—indexed for Medline], 62:415-425.

Camelliti et al., "Structural and functional coupling of cardiac myocytes and fibroblasts," *Adv. Cardiol.*, 2006, PMID: 16646588 [PubMed—indexed for Medline], 42:132-149.

Cheng et al., "Spinal Cord Repair in Adult Paraplegic Rats: Partial Restoration of Hind Limb Function," *Science*, Jul. 26, 1996, 273:510-513.

"A Chinese procedure involving stem cell transplants is providing some very interesting results," Oct. 24, 2003, Canadian Paraplegic Association, accessed online on Sep. 29, 2006 at http://www.canparaplegic.org/national/level12.tpl?var1=story&var2=20031024154627, 2 pages.

Chou et al., "Quantitative Analysis of Dose-Effect Relationships: The Combined Effects of Multiple Drugs or Enzyme Inhibitors," *Ad. Enzyme Reg.*, 1984, 22:27-55.

CoDa Therapeutics, "CoDa Therapeutics Achieves Positive Phase 2 Efficacy of NEXAGON® in Chronic Venous Leg Ulcers," CoDa Therapeutics news release, May 25, 2010, and available at http://www.codatherapeutics.com/news-nexagon.html.

CoDa Therapeutics, "CoDa Therapeutics Announces Positive Results from Phase 2b Study of NEXAGON® in Chronic Venous Leg Ulcers," Press Release dated Jan. 8, 2013, San Diego, accessed on Aug. 22, 2013 at http://www.codatherapeutics.com/news-nexagon-8-1-13.html, 3 pages.

Coffey et al., "Molecular profiling and cellular localization of connexin isoforms in the rat ciliary epithelium," *Exp. Eye Res.*, 2002, PMID: 12123633 [PubMed—indexed for Medline], 75(1):9-21.

Collaborative Neuroscience, "Gel 'is helping wounds heal in half the time'/nexagon," The Spinal Cord Injury Project, Care Cure Community Postings, Oct. 20, 2003, and online at http://sci.rutgers.edu/forum/showthread.php?t=6653, 2 pages.

Common et al., "Functional studies of human skin disease- and deafness-associated Connexin 30 mutations," *Biochemical and Biophysical Research Communications*, 2002, 298:651-656.

Cook et al., "Gap Junctions in the vertebrate retina," *Microscopy Research and Technique*, 1995, 31:408-419.

Courtman et al., "Development of a pericardial acellular matrix biomaterial: biochemical and mechanical effects of cell extraction," *J. Biomed. Mater. Res.*, 1994, 28:655-666.

Coutinho et al., "Limiting wound extension by transient inhibition of connexin43 expression at the site of injury," *Brit. J. Plast. Surg.*, 2005, 58:658-667.

Coutinho et al., "Dynamic changes in connexin expression correlate with key events in the wound healing process," *Cell Biol. Int.*, 2003, 27:525-541.

Cronin et al., "Antisense delivery and protein knockdown within the intact central nervous system," *Frontiers in Bioscience*, Sep. 1, 2006, 11:2967-2975.

Dang et al., "The carboxy-tail of connexin-43 localizes to the nucleus and inhibits cell growth," *Molecular and Cellular Biochemistry*, Jan. 1, 2003, 242:35-38.

Darrow et al., "Expression of multiple connexins in cultured neonatal rat ventricular myocytes," *Circ. Res.*, 1995, 76:381-387.

Davidson, "Animal Models for Wound Repair," *Arch. Dermatol. Res.*, 1998, 290:S1-S11.

Davis et al., "Modulation of Connexin43 Expression: Effects on Cellular Coupling," *Journal of Cardiovascular Electrophysiology*, Feb. 1995, 6(2):103-114.

De Carvalho et al., "Conduction Defects and Arrhythmias in Chagas' Disease: Possible Role of Gap Junctions and Humoral Mechanisms," *Journal of Cardiovascular Electrophysiology*, Aug. 8, 1994, 5(8):686-698.

Devereaux et al., "A comprehensive set of sequence analysis programs for the Vax," *Nucleic Acids Research*, 1984, 12:387-395.

Devlin et al., "An ovine model of chronic stable heart failure," *Journal of Cardiac Failure*, 2000, 6(2):140-143.

Devries et al., "Hemi-gap-junction channels in solitary horizontal cells of the catfish retina," *Journal of Physiology*, 1992, 445:201-230.

De Vriese et al., "Effects of connexin-mimetic peptides on nitric oxide synthase- and cyclooxygenase-independent renal vasodilation," *Kidney Int.*, 2002, 61:177-185.

Di et al., "Oestriol and oestradiol increase cell to cell communication and connexin 43 protein expression in cultured human myometrial cells," *Molecular Human Reproduction*, 2001, 7(7):671-679.

Doughty, "Why Won't Some Wounds Heal?" *Advances in Skin & Wound Care*, Sep. 2004, 17(7):342.

Einarson et al., "Identification of Protein-Protein Interactions with Glutathione S-Transferase Fusion Proteins," *Protein-Protein Interactions: A Molecular Cloning Manual*, 2002, Chapter 4, Cold Spring Harbor Laboratory Press, pp. 37-57.

Einarson, "Detection of Protein-Protein Interactions Using the GST Fusion Protein Pulldown Technique," *Molecular Cloning: A Laboratory Manual*, 3rd Edition, vol. 3, 2001, Chapter 18, Protocol 3, Cold Spring Harbor Laboratory Press, pp. 18.55-18.59.

Evans et al., "Connexin mimetic peptides: specific inhibitors of gap-junctional intercellular communication," *Biochem. Soc. Trans.*, 2001, 29:606-612.

Ferrin et al., "Selective Cleavage of Human DNA: RecA-Assisted Restriction Endonuclease (RARE) Cleavage," *Science*, Dec. 6, 1991, 254:1494-1497.

Flower et al., "A new type of gap junction in the phylum Brachiopoda" *Cell Tissue Res.*, 1982, 227:231-234.

Fonseca et al. "Upregulation in astrocytic connexin 43 gap junction levels may exacerbate generalized seizures in mesial temporal lobe

(56) References Cited

OTHER PUBLICATIONS epilepsy," *Brain Research*, PMID: 11852037 [PubMed—indexed for Medline], 2002, 929:105-116.
Foote et al., "The Pattern of Disulfide Linkages in the Extracellular Loop Regions of Connexin 32 Suggests a Model for the Docking Interface of Gap Junctions," *Journal of Cell Biology*, 1998, 140(5):1187-1197.
Forge et al., "Gap junctions and connexin expression in the inner ear," *Gap junction-mediated intercellular signalling in health and disease*, Novartis Foundation Symposium, 1999, 219:134-156.
Forge et al., "Gap Junctions in the Inner Ear: Comparison of Distribution Patterns in Different Vertebrates and Assessment of Connexin Composition in Mammals" *The Journal of Comparative Neurology*, 2003, 467:207-231.
Forge et al., "Connexins and gap junctions in the inner ear," *Audiol. Neurootol.*, 2002, 7:141-145.
Forge et al., "The inner ear contains heteromeric channels composed of Cx26 and Cx30 and deafness-related mutations in Cx26 have a dominant negative effect on Cx30," *Cell Communication and Adhesion*, 2003, 10:341-346.
Franteseva et al., "Ischemia-Induced Brain Damage Depends on Specific Gap-Junctional coupling," *Journal of Cerebral Blood Flow and Metabolism*, Apr. 2002, 22(4):453-462.
Fraser et al., "Selective disruption of gap junctional communication interferes with a patterning process in hydra," *Science*, Jul. 3, 1987, PMID: 3037697 [PubMed—indexed for Medline], 237:49-55.
Garcia-Dorada et al., "Gap Junction Uncoupler Heptanol Prevents Cell-to-Cell Progression of Hypercontracture and Limits Necrosis During Myocardial Reperfusion," *Circulation*, Nov. 18, 1997, 96(10):3579-3586.
Giepmans et al., "Interaction of c-Src with gap junction protein connexin-43: Role in the regulation of cell-cell communication," *J. Biol. Chem.*, 2001, 276(11):8544-8549.
Gouger et al.,"Wounding Alters Epidermal Connexin Expression and Gap Junction-mediated Intercellular Communication," *Molecular Biology of the Cell*, 1995, 6:1491-1501.
Goodenough et al., "Topological Distribution of Two Connexin32 Antigenic Sites in Intact and Split Rodent Hepatocyte Gap Junctions," *J. Cell Biol.*, 1988, 107:1817-1824.
Görbe et al., "In differentiating prefusion myoblasts connexin43 gap junction coupling is upregulated before myoblast alignment then reduced in post-mitotic cells," *Histochem. Cell Biol.*, 2006, 125:705-716.
Görbe et al., "Transient upregulation of connexin 43 gap junction coupling in myoblasts may synchronize cell cycle control preceding syncytial fusion during skeletal muscle differentiation," *Histochem Cell Biol.*, 2005, 123:573-583.
Gourdie et al., "Evidence for a distinct gap-junctional phenotype in ventricular conduction tissues of the developing and mature avian heart," *Circulation Research*, Feb. 1993, PMID: 8380357 [PubMed—indexed for Medline], 72(2):278-289.
Gourdie et al., "Immunolabelling patterns of gap junction connexins in the developing and mature rat heart," *Anat. Embryol. (Berl.)*, 1992, PMID: 1319120 [PubMed—indexed for Medline], 185(4):363-378.
Gourdie et al., "Gap junction distribution in adult mammalian myocardium revealed by an anti-peptide antibody and laser scanning confocal microscopy," *Journal of Cell Science*, 1991, PMID: 1661743 [PubMed—indexed for Medline], 99(1):41-55.
Gourdie et al., "Cardiac gap junctions in rat ventricle: localization using site-directed antibodies and laser scanning confocal microscopy," *Cardioscience*, Mar. 1990, PMID: 1966373 [PubMed—indexed for Medline], 1(1):75-82.
Gourdie et al., "The spatial distribution and relative abundance of gap-junctional connexin40 and connexin43 correlate to functional properties of components of the cardiac atrioventricular conduction system," *Journal of Cell Science*, 1993, 105:985-991.
Gourdie et al., "The unstoppable connexin43 carboxyl-terminus—New roles in gap junction organization and wound healing," *Annals of the New York Academy of Sciences*, 2006, 1080:49-62.

Grazul-Bilska et al., "Transfection of bovine luteal cells with gap junctional protein connexin 43 (Cx43) antisense oligonucleotide affects progesterone secretion," 31st Annual Meeting of the Society for the Study of Reproduction, Aug. 8-11, 1998 (Abstract), *Biology of Reproduction*, 58:78.
Green et al., "Spatiotemporal depletion of connexins using antisense oligonucleotides," *Methods in Molecular Biology: Connexin Methods and Protocols*, Bruzzone et al., eds., 2001, Humana Press Inc., Totowa, NJ, pp. 175-185.
Green et al., "Expression of the connexin43 gap junctional protein in tissues at the tip of the chick limb bud is related to the epithelial-mesenchymal interactions that mediate morphogenesis," *Developmental Biology*, 1994, PMID: 8293868 [PubMed—indexed for Medline],161:12-21.
Green et al., "Analysis of the rat liver gap junction protein; clarification of anomalies in its molecular size," *Proc. R. Soc. Lond. B. Biol. Sci.*, Mar. 22, 1988, PMID: 2898146 [PubMed—indexed for Medline],233(1271):165-174.
Green et al., "Validation of immunohistochemical quantification in confocal scanning laser microscopy; a comparative assessment of gap junction size with confocal and ultrastructural techniques," *The Journal of Histochemistry and Cytochemistry*, Sep. 1993, PMID: 8354875 [PubMed—indexed for Medline],41(9):1339-1349.
Green et al., "Connexon rearrangement in cardiac gap junctions: evidence for cytoskeletal control?" *Cell and Tissue Research*, 1984, PMID: 6090023 [PubMed—indexed for Medline],237:185-186.
Green et al., "Gap junction connexon configuration in rapidly frozen myocardium and isolated intercalated disks," *Journal of Cell Biology*, 1984, 99(2):453-463.
Green et al., "Distribution and role of gap junctions in normal myocardium and human ischaemic heart disease," *Histochemistry*, 1993, 99(2):105-120.
Green, "Evidence mounts for the role of gap junctions during development," *BioEssays*, Jan. 1988, 8(1):7-10.
Hall, "Gel 'is helping wounds heal in half the time,'" *Telegraph UK*, Oct. 20, 2003, accessed online at http://www.telegraph.co.uk/news/main.jhtmil?xml=/news/2003/10/20/nge120.x m1&sSheet= . . . , 2 pages.
Hardy et al., "Cell death (Apoptosis) in human blastocysts," *An Atlas of Human Blastocysts*, Chapter. 9, Veeck et al., eds., 2003, CRC Press, pp. 185-202.
Hardy et al., "Expression of intercellular junctions during the preimplantation development of the human embryo," *Molecular Human Reproduction*, 1996, 2(8):621-632.
Harfst et al., "Cardiac myocyte gap junctions; evidence for a major connexon protein with an apparent relative molecular mass of 70,000," *J. Cell Sci.*, Aug. 1990, 96(4):591-604.
Henikoff et al., "Amino acid substitution matrices from protein blocks," *Proc. Natl. Acad. Sci. USA*, 1992, 89:10915-10919.
Hennemann et al., "Molecular cloning of mouse connexins26 and -32: similar genomic organization but distinct promoter sequences of two gap junction genes," *European Journal of Cell Biology*, 1992, 58(1):81-89.
Hermanson, ed., *Bioconjugate Techniques*, Chapters 2 and 17, 1996, Academic Press, pp. 137-166 and 639-671.
Ho et. al., "Ischemic Optic Neuropathy Following Spine Surgery," *Journal of Neurosurgical Anesthesiology*, Jan. 2005, 17(1):38-44.
Hodgins, "Connecting Wounds with Connexins," *The Journal of Investigative Dermatology*, 2004, 122(5):ix-x.
Janes, "Speed healing," *Unlimited*, Dec. 1, 2004, accessed online at http://unlimited.co.nz/unlimited.nsf/ulfuture/250EA628CE599A70CC256F6B00046325, 67:1-5.
Jen et al., "Suppression of Gene Expression by Targeted Disruption of Messenger RNA: Available Options and Current Strategies," *Stem Cells*, 2000, 18:307-319.
Karlin et al., "Applications and statistics for multiple high-scoring segments in molecular sequences," *Proc. Natl. Acad. Sci. USA*, 1993, 90:5873-5787.
Lampe et al., "Cellular Interaction of Integrin α3β1 with Laminin 5 Promotes Gap Junctional Communication," *The Journal of Cell Biology*, Dec. 14, 1998, Downloaded from jcb.rupress.org on Mar. 12, 2010, 143(6):1735-1747.

(56) References Cited

OTHER PUBLICATIONS

Laux-Fenton et al., "Connexin expression patterns in the rat cornea: molecular evidence for communication compartments," *Cornea*, 2003, PMID: 12827052 [PubMed—indexed for Medline], 22(5):457-464.
Law, et al., "Knockdown of connexin43-mediated regulation of the zone of polarizing activity in the developing chick limb leads to digit truncation," *Development. Growth Differ.*, 2002, 44:537-547.
laxat.com, "Nice blurb on biologics on cbsnews.com," Sep. 9, 2006, accessed online at http;//www.laxat.com/Nice-blurb-on-biologics-on-cbsnews-com-1219610.html, 4 pages.
Leybaert et al., "Connexin Channels, Connexin Mimetic Peptides and ATP Release," *Cell Commun. Adhes.*, 2003, 10:251-257.
Li et al., "Properties and regulation of gap junctional hemichannels in the plasma membranes of cultured cells," *Journal of Cell Biology*, 1996, 134(4):1019-1030.
Lin et al., "v-Src phosphorylation of connexin 43 on Tyr247 and Tyr265 disrupts gap junctional communication," *The Journal of Cell Biology*, Aug. 20, 2001, 154(4):815-827.
Makarenkova et al., "Fibroblast growth factor 4 directs gap junction expression in the mesenchyme of the vertebrate limb bud," *The Journal of Cell Biology*, Sep. 8, 1997, Downloaded from jcb.org on Jul. 26, 2006, 138(5):1125-1137.
Malone et al., "Detergent-extracted small-diameter vascular prostheses," *J. Vasc. Surg.*, 1984, 1:181-191.
Martin et al., "Wound Healing-Aiming for Perfect Skin Regeneration," *Science*, 1997, Downloaded from www.sciencemag.org on Mar. 12, 2010, 276:75-81.
Marziano et al., "Mutations in the gene for connexin 26 (GJB2) that cause hearing loss have a dominant negative effect on connexin 30," *Human Molecular Genetics*, 2003, 12(8):805-812.
McGonnell et al., "Connexin43 Gap Junction Protein Plays an Essential Role in Morphogenesis of the Embryonic Chick Face," *Developmental Dynamics*, 2001, 222:420-438.
Medical Futures—Innovation Awards, May 26, 2006, accessed online at http;//www.medicalfutures.co.uk/runner php?txtWin=1, 1 page.
Merrifield, "Solid Phase Peptide Synthesis—I: The Synthesis of a Tetrapeptide," *J. Am. Chem. Soc.*, 1963, 85:2149-2154.
Meyer et al., "Inhibition of Gap Junction and Adherens Junction Assembly by Connexin and A-CAM Antibodies," *J. Cell Biol.*, 1992, 119:179-189.
Moore et al., "Selective block of gap junction channel expression with connexin-specific antisense oligodeoxynucleotides," *American Journal of Physiology*, Nov. 1994, 265(1):C1371-C1388.
Mori et al., "Acute downregulation of connexin43 at wound sites leads to a reduced inflammatory response, enhanced keratinocyte proliferation and wound fibroblast migration," *Journal of Cell Science*, Dec. 2006, 119(24):5193-5203.
Nadarajah et al., "Basic FGF increases communication between cells of the developing neocortex," *The Journal of Neuroscience*, Oct. 1, 1998, 18(19):7881-7890.
Nakano et al., "Changes in the expression of the gap junction protein connexin43 during wound healing of the rat corneal endothelium," *Bioimages*, 2004, 12(2-4):118.
Nakano et al., "Connexin43 Knockdown Accelerates Wound Healing but Inhibits Mesenchymal Transition after Corneal Endothelial Injury In Vivo," *Investigative Ophthalmology & Visual Science*, Jan. 2008, 49(1):93-104.
Nickel et al., "Molecular and functional characterization of gap junctions in the avian inner ear," *The Journal of Neuroscience*, 2006, 26(23):6190-6199.
Notice of Preliminary Rejection dated Jun. 2, 2014, from corresponding Korean Patent Application No. 10-2009-7014484, 14 total pages.
Notification of Reexamination mailed on Apr. 16, 2014 from related Chinese Patent Application No. 200780051207.X, 24 total pages.
Office Action mailed on Jul. 3, 2014, in corresponding Japanese Patent Application No. 2013-117401, 4 total pages.

Pearson et al., "Gap junctions modulate interkinetic nuclear migration in retinal progenitor cells," *The Journal of Neuroscience*, Nov. 16, 2005, 25(46):10803-10814.
Peters et al., "Cardiac arrhythmogenesis and the gap junction," *J. Mol. Cell Cardiol.*, 1995, 27(1):37-44.
Peters et al., "Reduced content of connexin43 gap junctions in ventricular myocardium from hypertrophied and ischemic human hearts," *Circulation*, Sep. 1993, 88(3):864-875.
Peters et al., "The Wolff-Parkinson-White syndrome: the cellular substrate for conduction in the accessory atrioventricular pathway," *European Heart Journal*, 1994, 15(7):981-987.
Peters et al., "Spatiotemporal relation between gap junctions and fascia adherens junctions during postnatal development of human ventricular myocardium," *Circulation*, Aug. 1994, 90(2):713-725.
Poladia et al., "Innervation and connexin isoform expression during diabetes-related bladder dysfunction: early structural vs. neuronal remodeling," *Acta Diabetol.*, 2005, 42:147-152.
Qiu et al., "Accelerated rate of wound repair by targeting connexin 43 expression," *Current Biology*, Sep. 30, 2003, 13:1697-1703.
Qiu et al., "Dynamic changes in connexin expression correlate with key events in the wound healing process," *Cell Biology International*, 2003, 27:525-541.
Qiu et al., "Targeting connexin43 expression accelerates the rate of wound repair," *Current Biology*, Sep. 30, 2003, 13(19):1967-1703.
Ruch et al., "Inhibition of Gap Junctional Intercellular Communication and Enhancement of Growth in BALBk 3T3 Cells Treated With Connexin43 Antisense Oligonucleotides," *Molecular Carcinogenesis*, 1995, 14:269-274.
Ratkay-Traub et al., "Regeneration of rabbit cornea following excimer laser photorefractive keratectomy; a study on gap junctions, epithelial junctions and epidermal growth factor receptor expression in correlation with cell proliferation," *Experimental Eye Research*, 2001, 73(5):291-302.
Rennick et al., "Expression of connexin43 gap junctions between cultured vascular smooth muscle cells is dependent upon phenotype," *Cell and Tissue Research*, 1993, 271(2):323-332.
Roberts et al., "Follicle-stimulating hormone affects metaphase I chromosome alignment and increases aneuploidy in mouse oocytes matured in vitro," *Biology of Reproduction*, 2005, Published online before print Sep. 15, 2004, 72:107-118.
Rosendaal et al., "Up-regulation of the connexin43+ gap junction network in haemopoietic tissue before the growth of stem cells," *Journal of Cell Science*, 1994, 107(1):29-37.
Rouach et al., "Hydrogen Peroxide Increases Gap Junctional Communication and Induces Astrocyte Toxicity: Regulation by Brain Macrophages," *GLIA*, 2004, 45(1):28-38.
Rozenthal et al., "Stable Transfection With Connexin43 Inhibits Neuronal Differentiation of PC12 Cells," *Society for Neuroscience Abstracts*, Society for Neuroscience, Oct. 1997, 23(1-3), 25:22.
Saitongdee et al., "Levels of gap junction proteins in coronary arterioles and aorta of hamsters exposed to cold and during hibernation and arousal," *Journal of Histochemistry & Cytochemistry*, 2004, 52(5):603-615.
Saitongdee et al., "Increased Connexin43 Gap Junction Protein in Hamster Cardiomyocytes During Cold Acclimatization and Hibernation," *Cardiovascular Research*, 2000, 47:108-115.
Salameh et al., "Pharmacology of Gap junctions: New pharmacological targets for treatment of arrhythmia, seizure and cancer?" *Biochimica et Biophysica Acta*, 2005, 1719(1-2):36-58.
Santoro et al., "A General Purpose RNA-Cleaving DNA Enzyme," *Proc. Natl. Acad. Sci. USA*, Apr. 1997, 94:4262-4266.
Scatchard et al., "Molecular Interaction," *Annals of the New York Academy of Sciences*, 1949, 51(4):660-672.
Schuck, "Reliable determination of binding affinity and kinetics using surface plasmon resonance biosensors," *Current Opinion in Biotechnology*, 1997, 8(4):498-502.
Serena et al., "Acceleration of Venous Ulcer Healing Using a Topical Connexin43 Antisense Compound: Phase 2 Results," *Symposium on Advanced Wound Care*, Apr. 14-17, 2011, Abstract, pp. W57-W58.
Severs et al., "Intercellular junctions and the application of microscopical techniques: the cardiac gap junction as a case model," *Journal of Microscopy*, Mar. 1993, 169(3):299-328.

(56) References Cited

OTHER PUBLICATIONS

Severs et al., "Fate of gap junctions in isolated adult mammalian cardiomyocytes," *Circulation Research*, Jul. 1989, 65(1):22-42.
Severs et al., "Integrity of the dissociated adult cardiac myocyte: gap junction tearing and the mechanism of plasma membrane resealing," *Journal of Muscle Research and Cell Motility*, 1990, 11(2):154-166.
Sheehan et al., "Percentage Change in Wound Area of Diabetic Foot Ulcers Over a 4-Week Period Is a Robust Predictor of Complete Healing in a 12-week Prospective Trial," *Diabetes Care*, Jun. 2003, 26(6):1879-1882.
Shi et al., "Supplemental L-arginine enhances wound healing in diabetic rats," *Wound Repair and Regeneration*, May-Jun. 2003, 11(3):198-203.
Shotton et al., "The Effectiveness of Treatments of Diabetic Autonomic Neuropathy is Not the Same in Autonomic Nerves Supplying Different Organs," *Diabetes*, Jan. 2003, 52:157-164.
Sibbald et al., "Venous leg ulcers," in *Chronic Wound Care: A Clinical Source Book for Healthcare Professionals, 4th edition*, Krasner et al., eds., 2007, HMP Communications, pp. 429-442.
Singh et al., "Inhibition of connexin 43 synthesis by antisense RNA in rat glioma cells," *Cytobios*, 1997, 91:103-123.
Smith et al., "Altered patterns of gap junction distribution in ischemic heart disease: An immunohistochemical study of human myocardium using laser scanning confocal microscopy," *American Journal of Pathology*, Oct. 1991, 139(4):801-821.
Spanos et al., "Caspase activity and expression of cell death genes during human preimplantation embryo development," *Journal of Reproduction*, 2002, 124:353-363.
Stein et al., eds., *Applied Antisense Oligonucleotide Technology*, Chapters 7, 10, and 22, 1998, Wiley-Liss.
Stewart et al., *Solid Phase Peptide Synthesis*, 1969, W.H. Freeman Co., San Francisco, pp. 71-135.
Stilinovic et al., "Texture analysis of collagen fibers in scar tissue," *Proc. Image Vision Computing New Zealand*, Nov. 21, 2004, pp. 185-190.
*Summary of Safety and Effectiveness Data* for "Apligraf™," Jun. 20, 2000, accessed online at http://www.accessdata.fda.gov/cdrh_docs/pdf/P950032S016b.pdf, 18 pages.
UCL Media Relations, "News bio-active gel cuts wound healing time in half," Oct. 20, 2003, University College London, accessed online Sep. 29, 2006 at http://www.ucl.ac.uk/media/library/nexagon0, 2 pages.
UCL News, "Wound-healing technology shortlisted for award," University College London, accessed online Sep. 27, 2006 at http://www.ucl.ac.uk/news-archive/archive/2003/october-003/latest/newsitem.shtml?0309 . . . , 1 page.
U.S. Department of Health and Human Services Food and Drug Administration, "Guidance for Industry: Chronic Cutaneous Ulcer and Burn Wounds—Developing Products for Treatment," Jun. 2006.
Vikis et al., "Glutathione-S-Transferase-Fusion Based Assays for Studying Protein-Protein Interactions," from *Methods in Molecular Biology, Volume 261: Protein-Protein Interactions: Methods and Applications*, Fu, ed., 2004, Humana Press, Totown, NJ, pp. 175-186.
Vis et al., "Connexin expression in Huntington's diseased human brain," *Cell Biology International*, 1998, 22(11-12):837-847.
Wang et al., "Gap junction expression in diabetic rat wound healing ," *Proceedings of the Anatomical Society of Great Britain and Ireland*, Oct. 2006, 209(4):569.

Wang et al., "Targeting connexin43 expression accelerates the rate of skin and diabetic wound repair," *Journal of Biotechnology*, Sep. 2007, 131(2):S64.
Wang, Wound Healing and Tissue Repair, Section 2, Dec. 1998, Shandong Science and Technology Press, 1st Edition, pp. 6-28 (translation not available).
Wang, Wound Healing and Tissue Repair, Section 5, Dec. 1998, Shandong Science and Technology Press, 1st Edition, pp. 137-161 (translation not available).
Wei et al., "Connexins and Cell Signaling in Development and Disease[1]," *Annu. Rev. Cell Dev. Biol.*, 2004, 20:811-838.
"Welcome to the lab of David Becker and Jeremy Cook," Becker/Cook Lab, May 26, 2006, accessed online at http://www.anat.ucl.ac.uk/research/becker/people.htm , 5 pages.
Willecke et al., "Structural and functional diversity of connexin genes in the mouse and human genome," *Biological Chemistry*, May 2002, 383(5):725-737.
Wilson et al., "Acellular Matrix Allograft Small Caliber Vascular Prostheses," *Trans. Am. Soc. Artif. Intern.*, 1990, 36:340-343.
Witte et al., "Nitric Oxide Enhances Experimental Wound Healing in Diabetes," *British Journal of Surgery*, 2002, 89:1594-1601.
Wright et al., "Stage-specific and differential expression of gap junctions in the mouse ovary: connexin-specific roles in follicular regulation," *Journals of Reproduction and Fertility*, 2001, 121:77-88.
Yang et al., "Synthesis and biological activities of potent peptideomimetics selective for somatostatin receptor subtype 2," *Proc. Natl. Acad. Sci. USA*, 1998, 95(18):10836-10841.
Zhang et al., "Differential connexin expression in preglomerular and postglomerular vasculature: Accentuation during diabetes," *Kidney International*, 2005, 68:1171-1185.
Zhang et al., "Use of surface plasmon resonance for the measurement of low affinity binding interactions between HSP72 and measles virus nucleocapsid protein," *Biological Procedures Online*, 2003, 5(1): 170-181.
Zimmer et al., "Topological analysis of the major protein in isolated intact rat liver gap junctions and gap junction-derived single membrane structures," *Journal of Biological Chemistry*, Jun. 5, 1987, 262(16):7751-7763.
AU2007333535 Examination Report mailed Dec. 10, 2012.
U.S. Appl. No. 12/001,498, Requirement for Restriction/Election, mailed Apr. 22, 2009.
EP 05016736.0 EP Search Report & Opinion mailed Dec. 19, 2005.
PCT/US2007/025446 Written Opinion, mailed Jun. 16, 2009.
EP07853353.6 Communication pursuant to article 94(3) mailed Aug. 20, 2010.
EP08860470.7 Examination Report mailed Jan. 19, 2011.
CN200780051207 First Office Action mailed Nov. 10, 2011.
CN200780051207 Second Office Action mailed Sep. 28, 2012.
CN200880126536.0 First Office Action mailed Jul. 22, 2011.
CN200880126536.0 Second Office Action mailed Mar. 31, 2012.
PCT/US2008/013656 International Search Report and Written Opinion mailed Jun. 15, 2009.
PCT/US2008/013655 International Search Report and Written Opinion mailed Aug. 8, 2009.
Examination Report dated Feb. 5, 2013 in corresponding European Patent Application No. 07853353.6, 5 pages.
Kretz M, et al. Altered connexin expression and wound healing in the epidermis of connexin-deficient mice. J Cell Sci. 2003;116:3443-3452.
Official Action in Japanese Application No. 2015-000248, dated Aug. 31, 2016, in 4 pages.

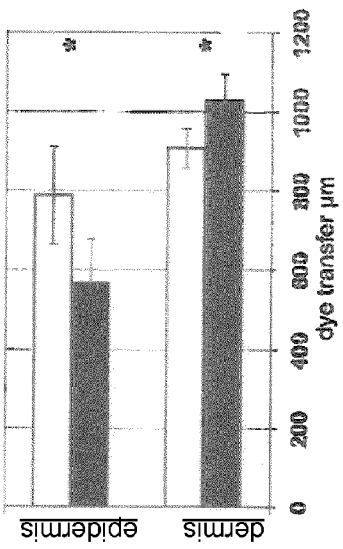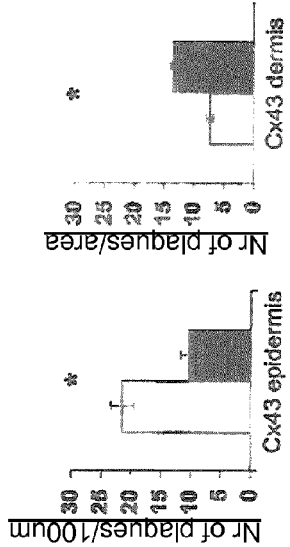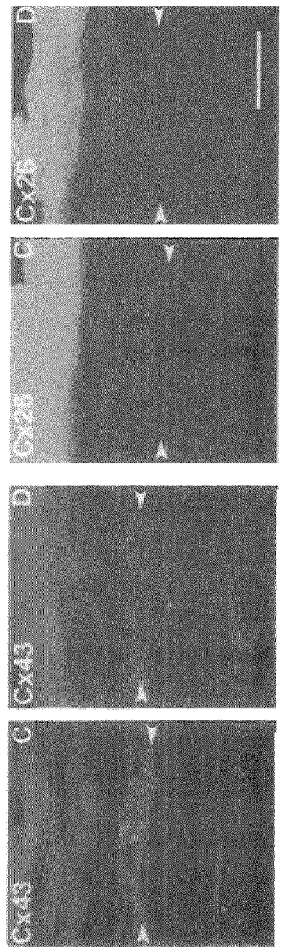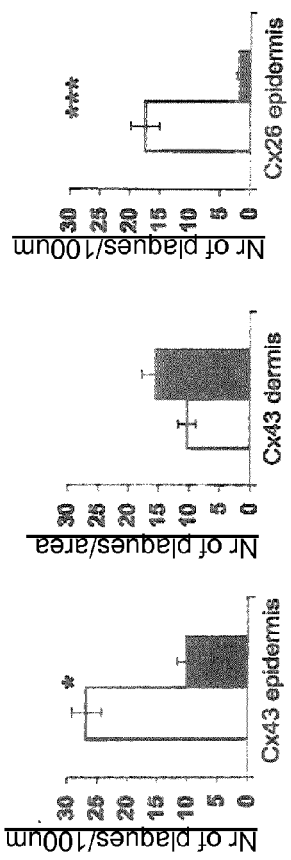
FIG. 1A
FIG. 1B
FIG. 1C
FIG. 1D

FIG. 2A
FIG. 2B
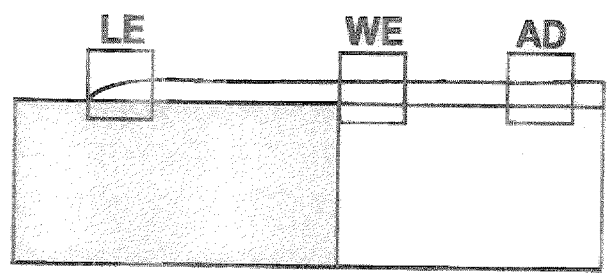
| dpw | C | D (%) |
|---|---|---|
| 1 | 7.5 | 2.5 |
| 2 | 15.7 | 6.1 |
| 5 | 41.0 | 27.4 |
FIG. 2C
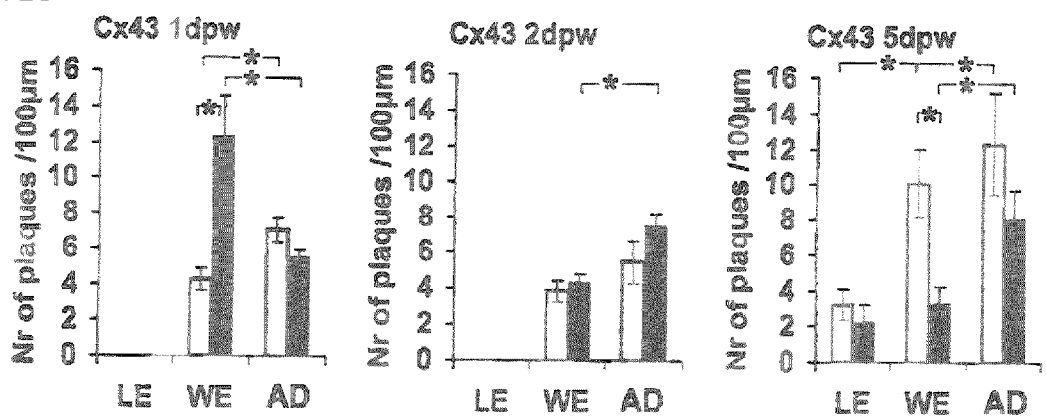
FIG. 2D
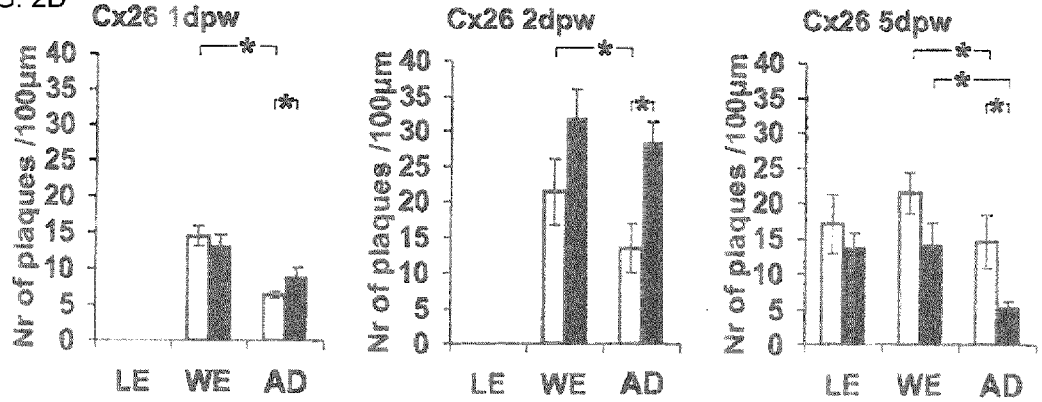

Cx43

Cx26

SEQUENCE LISTING

<160> NUMBER OF SEQ ID NOS: 14

<210> SEQ ID NO 1
<211> LENGTH: 30
<212> TYPE: DNA
<213> ORGANISM: Artificial
<220> FEATURE:
<223> OTHER INFORMATION: synthetic oligonucleotide

<400> SEQUENCE: 1
gtaattgcgg caagaagaat tgtttctgtc                                      30

<210> SEQ ID NO 2
<211> LENGTH: 30
<212> TYPE: DNA
<213> ORGANISM: artificial
<220> FEATURE:
<223> OTHER INFORMATION: synthetic oligonucleotide

<400> SEQUENCE: 2
gtaattgcgg caggaggaat tgtttctgtc                                      30

<210> SEQ ID NO 3
<211> LENGTH: 30
<212> TYPE: DNA
<213> ORGANISM: artificial
<220> FEATURE:
<223> OTHER INFORMATION: synthetic oligonucleotide

<400> SEQUENCE: 3
ggcaagagac accaaagaca ctaccagcat                                      30

<210> SEQ ID NO 4
<211> LENGTH: 27
<212> TYPE: DNA
<213> ORGANISM: artificial
<220> FEATURE:
<223> OTHER INFORMATION: synthetic oligonucleotide

<400> SEQUENCE: 4
tcctgagcaa tacctaacga acaaata                                         27

<210> SEQ ID NO 5
<211> LENGTH: 20

-continued

```
<212> TYPE: DNA
<213> ORGANISM: artificial
<220> FEATURE:
<223> OTHER INFORMATION: synthetic oligonucleotide

<400> SEQUENCE: 5
catctccttg gtgctcaacc                                              20

<210> SEQ ID NO 6
<211> LENGTH: 20
<212> TYPE: DNA
<213> ORGANISM: artificial
<220> FEATURE:
<223> OTHER INFORMATION: synthetic oligonucleotide

<400> SEQUENCE: 6
ctgaagtcga cttggcttgg                                              20

<210> SEQ ID NO 7
<211> LENGTH: 21
<212> TYPE: DNA
<213> ORGANISM: Artificial
<220> FEATURE:
<223> OTHER INFORMATION: synthetic oligonucleotide

<400> SEQUENCE: 7
ctcagatagt ggccagaatg c                                            21

<210> SEQ ID NO 8
<211> LENGTH: 20
<212> TYPE: DNA
<213> ORGANISM: artificial
<220> FEATURE:
<223> OTHER INFORMATION: synthetic oligonucleotide

<400> SEQUENCE: 8
ttgtccaggt gactccaagg                                              20

<210> SEQ ID NO 9
<211> LENGTH: 25
<212> TYPE: DNA
<213> ORGANISM: artificial
<220> FEATURE:
<223> OTHER INFORMATION: synthetic oligonucleotide

<400> SEQUENCE: 9
cgtccgagcc cagaaagatg aggtc                                        25

<210> SEQ ID NO 10
<211> LENGTH: 19
<212> TYPE: DNA
<213> ORGANISM: artificial
<220> FEATURE:
<223> OTHER INFORMATION: synthetic oligonucleotide

<400> SEQUENCE: 10
agaggcgcac gtgagacac                                               19

<210> SEQ ID NO 11
<211> LENGTH: 19
<212> TYPE: DNA
<213> ORGANISM: artificial
<220> FEATURE:
<223> OTHER INFORMATION: synthetic oligonucleotide

<400> SEQUENCE: 11
```
tgaagacaat gaagatgtt                                              19

<210> SEQ ID NO 12
<211> LENGTH: 25
<212> TYPE: DNA
<213> ORGANISM: artificial
<220> FEATURE:
<223> OTHER INFORMATION: synthetic oligonucleotide

<400> SEQUENCE: 12
tttcttttct atgtgctgtt ggtga                                       25

<210> SEQ ID NO 13
<211> LENGTH: 1314
<212> TYPE: DNA
<213> ORGANISM: Homo sapiens

<400> SEQUENCE: 13
ggcttttagc gtgaggaaag taccaaacag cagcggagtt ttaaacttta aatagacagg    60
tctgagtgcc tgaacttgcc ttttcatttt acttcatcct ccaaggagtt caatcacttg   120
gcgtgacttc actacttta agcaaaagag tggtgcccag caacatggg tgactggagc    180 gccttaggca aactccttga caaggttcaa gcctactcaa ctgctggagg aaggtgtgg    240 ctgtcagtac ttttcatttt ccgaatcctg ctgctggga cagcggttga gtcagcctgg    300
ggagatgagc agtctgcctt tcgttgtaac actcagcaac ctggttgtga aaatgtctgc    360
tatgacaagt ctttcccaat ctctcatgtg cgcttctggg tcctgcagat catatttgtg    420
tctgtaccca cactcttgta cctggctcat gtgttctatg tgatgcgaaa ggaagagaaa    480
ctgaacaaga aagaggaaga actcaaggtt gcccaaactg atggtgtcaa tgtggacatg    540
cacttgaagc agattgagat aaagaagttc aagtacggta ttgaagagca tggtaaggtg    600
aaaatgcgag gggggttgct gcgaacctac atcatcagta tcctcttcaa gtctatcttt    660
gaggtggcct tcttgctgat ccagtggtac atctatggat tcagcttgag tgctgtttac    720
acttgcaaaa gagatccctg cccacatcag gtggactgtt tcctctctcg ccccacggag    780
aaaaccatct tcatcatctt catgctggtg gtgtccttgg tgtccctggc cttgaatatc    840
attgaactct tctatgtttt cttcaagggc gttaaggatc gggttaaggg aaagagcgac    900
ccttaccatg cgaccagtgg tgcgctgagc cctgccaaag actgtgggtc tcaaaaatat    960
gcttatttca atggctgctc ctcaccaacc gctcccctct cgcctatgtc tcctcctggg   1020
tacaagctgg ttactggcga cagaaacaat tcttcttgcc gcaattacaa caagcaagca   1080
agtgagcaaa actgggctaa ttacagtgca gaacaaaatc gaatggggca ggcgggaagc   1140
accatctcta actcccatgc acagcctttt gatttcccg atgataacca gaattctaaa   1200
aaactagctg ctggacatga attacagcca ctagccattg tggaccagcg accttcaagc   1260
agagccagca gtcgtgccag cagcagacct cggcctgatg acctggagat ctag         1314

<210> SEQ ID NO 14
<211> LENGTH: 1149
<212> TYPE: DNA
<213> ORGANISM: Homo sapiens

<400> SEQUENCE: 14
atgggtgact ggagcgcctt aggcaaactc cttgacaagg ttcaagccta ctcaactgct    60
ggagggaagg tgtggctgtc agtactttc attttccgaa tcctgctgct ggggacagcg   120
gttgagtcag cctgggggaga tgagcagtct gcctttcgtt gtaacactca gcaacctggt   180

```
tgtgaaaatg tctgctatga caagtctttc ccaatctctc atgtgcgctt ctgggtcctg    240
cagatcatat ttgtgtctgt acccacactc ttgtacctgg ctcatgtgtt ctatgtgatg    300
cgaaaggaag agaaactgaa caagaaagag gaagaactca aggttgccca aactgatggt    360
gtcaatgtgg acatgcactt gaagcagatt gagataaaga agttcaagta cggtattgaa    420
gagcatggta aggtgaaaat gcgagggggg ttgctgcgaa cctacatcat cagtatcctc    480
ttcaagtcta tctttgaggt ggccttcttg ctgatccagt ggtacatcta tggattcagc    540
ttgagtgctg tttacacttg caaaagagat ccctgcccac atcaggtgga ctgtttcctc    600
tctcgcccca cggagaaaac catcttcatc atcttcatgc tggtggtgtc cttggtgtcc    660
ctggccttga atatcattga actcttctat gttttcttca agggcgttaa ggatcgggtt    720
aagggaaaga gcgaccctta ccatgcgacc agtggtgcgc tgagccctgc caaagactgt    780
gggtctcaaa aatatgctta tttcaatggc tgctcctcac caaccgctcc cctctcgcct    840
atgtctcctc ctgggtacaa gctggttact ggcgacagaa acaattcttc ttgccgcaat    900
tacaacaagc aagcaagtga gcaaaactgg gctaattaca gtgcagaaca aaatcgaatg    960
gggcaggcgg gaagcaccat ctctaactcc catgcacagc cttttgattt ccccgatgat   1020
aaccagaatt ctaaaaaact agctgctgga catgaattac agccactagc cattgtggac   1080
cagcgacctt caagcagagc cagcagtcgt gccagcagca gacctcggcc tgatgacctg   1140
gagatctag                                                           1149
```

IMPAIRED WOUND HEALING COMPOSITIONS AND TREATMENTS

RELATED APPLICATIONS

,This application is a continuation of U.S. patent application Ser. No. 13/764,674, filed on Feb. 11, 2013, which is a continuation of U.S. patent application Ser. No. 13/295, 020, filed on Nov. 11, 2011, which issued as U.S. Pat. No. 8,685,940 on Apr. 1, 2014, which is a continuation of U.S. application Ser. No. 12/001,498, filed on Dec. 11, 2007, which issued as U.S. Pat. No. 8,063,023 on Nov. 22, 2011, claims the benefit of U.S. Provisional Application Ser. No. 60/874,404, filed on Dec. 11, 2006, the contents of which are hereby incorporated by reference in its entirety.

FIELD

The inventions relate to gap junctions and to wounds and wound healing, in particular to wounds that do not heal at expected rates, such as delayed-healing wounds, incompletely healing wounds, chronic wounds, and dehiscent wounds.

BRIEF BACKGROUND

The following includes information that may be useful in understanding the present invention. It is not an admission that any of the information provided herein is prior art, or relevant to the presently described or claimed inventions, or that any publication or document that is specifically or implicitly referenced is prior art.

In humans and other mammals wound injury triggers an organized complex cascade of cellular and biochemical events that will in most cases result in a healed wound. An ideally healed wound is one that restores normal anatomical structure, function, and appearance at the cellular, tissue, organ, and organism levels. Wound healing, whether initiated by trauma, microbes or foreign materials, proceeds via a complex process encompassing a number of overlapping phases, including inflammation, epithelialization, angiogenesis and matrix deposition. Normally, these processes lead to a mature wound and a certain degree of scar formation. Although inflammation and repair mostly occur along a prescribed course, the sensitivity of the process is dependent on the balance of a variety of wound healing modulating factors, including for example, a complex network of regulatory cytokines and growth factors.

Gap junctions are cell membrane structures that facilitate direct cell-cell communication. A gap junction channel is formed of two connexons (hemichannels), each composed of six connexin subunits. Each hexameric connexon docks with a connexon in the opposing membrane to form a single gap junction. Gap junction channels are reported to be found throughout the body. Tissue such as the corneal epithelium, for example, has six to eight cell layers, yet expresses different gap junction channels in different layers with connexin 43 in the basal layer and connexin 26 from the basal to middle wing cell layers. In general, connexins are a family of proteins, commonly named according to their molecular weight or classified on a phylogenetic basis into alpha, beta, and gamma subclasses. At least 20 human and 19 murine isoforms have been identified. Different tissues and cell types are reported to have characteristic patterns of connexin protein expression and tissues such as cornea have been shown to alter connexin protein expression pattern following injury or transplantation (Qui et al. (2003) *Current Biology,* 13:1967-1703; Brander et al. (2004), *J. Invest Dermatol.* 122:1310-20).

It has been reported that abnormal connexin function may be linked to certain disease states (e.g. heart diseases) (A. C. de Carvalho, et al. (1994) *J Cardiovasc Electrophysiol* 5: 686). In certain connexin proteins, alterations in the turnover and trafficking properties may be induced by the addition exogenous agents which may affect the level of gap junctional intercellular communication (Darrow et al. (1995) *Circ Res* 76: 381; Lin et al. (2001) *J Cell Biol* 154(4):815). Antisense technology has also been reported for the modulation of the expression for genes implicated in viral, fungal and metabolic diseases. See, e.g., U.S. Pat. No. 5,166,195, (oligonucleotide inhibitors of HIV), U.S. Pat. No. 5,004,810 (oligomers for hybridizing to herpes simplex virus Vmw65 mRNA and inhibiting replication). See also U.S. Pat. No. 7,098,190 to Becker and Green (formulations comprising antisense nucleotides to connexins). Peptide inhibitors of gap junctions and hemichannels have also been reported. See for example, Berthoud et al. (2000) *Am J. Physiol. Lung Cell Mol. Physiol.* 279:L619-L622; Evans, W. H. and Boitano, S. *Biochem. Soc. Trans.* 29:606-612, and De Vriese A. S., et al. (2001) *Kidney Int.* 61:177-185. See also Green and Becker, WO2006/134494 ("Anti-connexin compounds and methods of use").

Despite advances in the understanding of the principles underlying the wound healing process, there remains a significant unmet need in suitable therapeutic options for wound care, including wounds that do not heal at expected rates, such as delayed-healing wounds, incompletely healing wounds, and chronic wounds. Such therapeutics compositions and treatments are described and claimed herein.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

The inventions generally relate to the use of an anti-connexin polynucleotide including, for example, a connexin antisense polynucleotide, and compositions and methods for the treatment of wounds that do not heal at expected rates, such as delayed-healing wounds, incompletely healing wounds, and chronic wounds.

The present invention provides for increases and improvements in the healing of wounds that do not heal at expected rates, such as delayed-healing wounds, incompletely healing wounds, and chronic wounds, through the use of one or more connexin antisense polynucleotides.

They also relate to the use of an anti-connexin polynucleotide in combination with dressings, bandages, matrices and coverings. In one aspect, the invention comprises a synthetic or naturally occurring wound healing matrix comprising an anti-connexin polynucleotide. In certain embodiments, the anti-connexin polynucleotide is a anti-connexin 43 polynucleotide, for example, an anti-connexin 43 polynucleotide. Preferred anti-connexin polynucleotides include anti-connexin oligodeoxynucleotides, such as anti-connexin 43 oligodeoxynucleotides.

They also relate to the use of anti-connexin polynucleotides, alone or in combination with dressings, bandages, matrices and coverings, in repeat applications, for example, once per week until healing is complete or as desired.

Compositions and methods of the invention that employ anti-connexin polynucleotides, including connexin antisense polynucleotides, are described and claimed.

In one aspect, the invention provides a pharmaceutical composition comprising one or more connexin antisense polynucleotides. Preferably, the pharmaceutical composition further comprises a pharmaceutically acceptable carrier, diluent or excipient. For example, the inventions include pharmaceutical compositions comprising (a) a therapeutically effect amount of a pharmaceutically acceptable connexin antisense polynucleotide and (b) a pharmaceutically acceptable carrier or diluent.

In one aspect, the invention includes pharmaceutical compositions, including topical delivery forms and formulations, which comprise a pharmaceutically acceptable carrier and therapeutically effective amounts of an anti-connexin polynucleotide, preferably a connexin antisense polynucleotide, and most preferably a connexin 43 antisense polynucleotide.

Examples of a connexin antisense polynucleotide include an anti-connexin oligodeoxynucleotide (ODN), including antisense (including modified and unmodified backbone antisense; e.g., a DNA antisense polynucleotide that binds to a connexin mRNA), RNAi, and siRNA polynucleotides.

Suitable connexin antisense polynucleotides include for example, antisense ODNs against connexin 43 (Cx43), connexin 26 (Cx26), connexin 37 (Cx37), connexin 30 (Cx30), connexin 31.1 (Cx31.1) and connexin 32 (Cx32). In certain embodiments, suitable compositions include multiple connexin antisense polynucleotides in combination, including for example, polynucleotides targeting Cx 43, 26, 30, and 31.1. Preferred connexin antisense polynucleotides target connexin 43.

Accordingly, in another aspect, the invention provides a formulation comprising at least one connexin antisense polynucleotide to a connexin protein together with a pharmaceutically acceptable carrier or vehicle. In one preferred form, the formulation contains polynucleotides to one connexin protein only. Most preferably, this connexin protein is connexin 43. Alternatively, the formulation contains oligodeoxynucleotides to more than one connexin protein.

The invention includes a formulation comprising a pharmaceutically acceptable anti-connexin polynucleotide, e.g., a connexin antisense polynucleotide, in an amount effective to promote wound healing in a subject having a chronic wound or a wound characterized by delayed healing, or other wounds that do not heal at expected rates. Such formulations include, for example, topical delivery forms and formulations. Preferred anti-connexin polynucleotides and connexin antisense polynucleotides are anti-connexin 43 polynucleotides and connexin 43 antisense polynucleotides.

Preferably, one of the connexin proteins to which oligodeoxynucleotides are directed is connexin 43. Other connexin proteins to which oligodeoxynucleotides are directed include connexin 26, connexin 31.1 and connexin 32.

Conveniently, the oligodeoxynucleotide to connexin 43 is selected from: GTA ATT GCG GCA AGA AGA ATT GTT TCT GTC (SEQ.ID.NO:1); GTA ATT GCG GCA GGA GGA ATT GTT TCT GTC (SEQ.ID.NO:2); GGC AAG AGA CAC CAA AGA CAC TAC CAG CAT (SEQ.ID.NO:3), a polynucleotide having at least about 70 percent homology with SEQ.ID.NOS:1, 2, or 3 or a polynucleotide which hybridizes to connexin 43 mRNA under conditions of medium to high stringency.

Conveniently, the oligodeoxynucleotide to connexin 26 is: TCC TGA GCA ATA CCT AAC GAA CAA ATA (SEQ.ID.NO:4), a polynucleotide having at least about 70 percent homology with SEQ.ID.NO: 4; or a polynucleotide which hybridizes to connexin 26 mRNA under conditions of medium to high stringency. Conveniently, the oligodeoxynucleotide to connexin 31.1 is: CGT CCG AGC CCA GAA AGA TGA GGT C (SEQ.ID.NO:9), a polynucleotide having at least about 70 percent homology with SEQ.ID.NO: 9; or a polynucleotide which hybridizes to connexin 31.1 mRNA under conditions of medium to high stringency. Conveniently, the oligodeoxynucleotide to connexin 32 is: TTT CTT TTC TAT GTG CTG TTG GTG A (SEQ.ID.NO:12), a polynucleotide having at least about 70 percent homology with SEQ.ID.NO: 12; or a polynucleotide which hybridizes to connexin 32 mRNA under conditions of medium to high stringency. Other connexin antisense polynucleotide sequences useful according to the methods of the present invention include:

```
                                            (SEQ ID NO: 5)
5' CAT CTC CTT GGT GCT CAA CC 3' (connexin 37)

(SEQ ID NO: 6)
5' CTG AAG TCG ACT TGG CTT GG 3' (connexin 37)

(SEQ ID NO: 7)
5' CTC AGA TAG TGG CCA GAA TGC 3' (connexin 30)

(SEQ ID NO: 8)
5' TTG TCC AGG TGA CTC CAA GG 3' (connexin 30)

(SEQ ID NO: 10)
5' AGA GGC GCA CGT GAG ACA C 3' (connexin 31.1)

(SEQ ID NO: 11)
5' TGA AGA CAA TGA AGA TGT T 3' (connexin 31.1)
```

The antisense polynucleotides are preferably administered topically (at and/or around the site to be treated). Suitably the antisense polynucleotides are combined with a pharmaceutically acceptable carrier, vehicle or diluent to provide a pharmaceutical composition.

Suitable pharmaceutically acceptable carriers or vehicles include any of those commonly used for topical administration. The topical formulation may be in the form, for example, of a cream, ointment, gel, emulsion, lotion, spray, foam or paint. The formulation of the invention may also be presented in the form of an impregnated dressing.

Preferably, the pharmaceutically acceptable carrier or vehicle is a gel, suitably a nonionic polyoxyethylene-polyoxypropylene copolymer gel, for example, a Pluronic gel, preferably Pluronic F-127 (BASF Corp.). This gel can be used as a liquid at low temperatures but rapidly sets at physiological temperatures, which can assist in confining the release of the anti-connexin oligonucleotide component to the site of application or immediately adjacent that site. Slow release gels in which the anti-connexin oligonucleotided is releases over time are preferred for topical application. Thus, the pharmaceutical composition may be formulated to provide sustained release of the anti-connexin polynucleotide, e.g., an antisense polynucleotide. Preferred anti-connexin polynucleotides and connexin antisense polynucleotides are anti-connexin 43 polynucleotides and connexin 43 antisense polynucleotides.

In another aspect, the invention includes methods for administering a therapeutically effective amount of one or more pharmaceutically acceptable connexin antisense polynucleotides formulated in a delayed release preparation, a slow release preparation, an extended release preparation, a controlled release preparation, and/or in a repeat action preparation to a subject with a wound characterized in whole or in part by delayed or incomplete wound healing, or other wound that does not heal at an expected rate. Such formulations are particularly advantageous for wounds that do not heal at expected rates, such as chronic wounds.

In certain other aspects, the inventions also relate to methods of using such compositions to treat subjects suffering from various diseases, disorders, and conditions associated with a wound that does not heal at the expected rate, such as a delayed-healing wound an incompletely healing wound, or a chronic wound. In yet another aspect, the invention includes methods for treating a subject having or suspected of having any diseases, disorders and/or conditions characterized in whole or in part by a chronic wound or delayed or incomplete wound healing, or other wound that does not heal at an expected rate. Such compositions include, for example, topical delivery forms and formulations. Preferred anti-connexin polynucleotides and connexin antisense polynucleotides are anti-connexin 43 polynucleotides and connexin 43 antisense polynucleotides.

In a further aspect, the invention includes transdermal patches, dressings, pads, wraps, matrices and bandages capable of being adhered or otherwise associated with the skin of a subject, said articles being capable of delivering a therapeutically effective amount of one or more pharmaceutically acceptable anti-connexin polynucleotides, e.g., connexin antisense polynucleotides.

The invention includes devices containing therapeutically effective amounts of one or more pharmaceutically acceptable anti-connexin polynucleotides, e.g., connexin antisense polynucleotides, for example, a rate-controlling membrane enclosing a drug reservoir and a monolithic matrix device. These devices may be employed for the treatment of subjects in need thereof as disclosed herein. Suitably the wound dressing or matrix is provided including the form of a solid substrate with an anti-connexin polynucleotide, e.g., a connexin antisense polynucleotide, dispersed on or in the solid substrate. In one embodiment the pharmaceutical product of the invention is provided in combination with a wound dressing or wound healing promoting matrix. Preferred anti-connexin polynucleotides and connexin antisense polynucleotides are anti-connexin 43 polynucleotides and connexin 43 antisense polynucleotides.

In yet a further aspect, the invention provides a method of promoting wound healing in a patient having a delayed healing wound or a chronic wound, which comprises the step of administering a formulation as defined herein to said wound in an amount effective to downregulate expression of connexin proteins at and immediately adjacent the site of said wound. Repeat applications are included within the invention. Downregulation of connexin 43 is preferred.

One aspect of the present invention is directed to a method of treating a subject having a delayed healing or chronic wound, or other wound that does not heal at an expected rate, which comprises administration of an effective amount of an anti-connexin polynucleotide, e.g., an anti-connexin polynucleotide. A suitable anti-connexin polynucleotide may be selected from the group consisting of a connexin antisense polynucleotide (e.g., a DNA antisense polynucleotide that binds to a connexin mRNA), an RNAi polynucleotide, and a siRNA polynucleotide. Preferred anti-connexin polynucleotides block or inhibit the expression of connexin 43. Repeat applications are included within the invention.

In one aspect, the present invention provides a method of treating a subject having a delayed or incompletely healing wound or a chronic wound, or other wound that does not heal at an expected rate, which comprises sustained administration of an effective amount of a connexin 43 antisense polynucleotide to the wound. Conveniently, the antisense polynucleotide is administered or delivered for at least about 0.5 hours, about 1-2 hours, about 2-4 hours, about 4-6 hours, or about 6-8 hours, but may be administered for longer, e.g., up to 24 hours, or more. 1-2 hour, 2-3 hour, and 4-8 hour application or delivery is presently preferred. According to one embodiment the subject is diabetic. In other embodiments, the patient has a diabetic ulcer, a diabetic foot ulcer, a vasculitic ulcer, a venous ulcer, a venous stasis ulcer, an arterial ulcer, a pressure ulcer, a decubitus ulcer, an infectious ulcer, a trauma-induced ulcer, a burn ulcer, ulcerations associated with pyoderma gangrenosum, or a mixed ulcer or ulcers. Repeat applications are included within the invention. Preferred are repeat applications until wound closure is seen to be proceeding, followed by a repeat application (or applications) in the event wound healing once again becomes stalled or delayed.

According to an alternate aspect, the present invention provides a method of treating a subject having a delayed or incompletely healing wound or a chronic wound, or other wound that does not heal at an expected rate, which comprises sustained administration to the wound (or to the area in or around a wound area) of a connexin 43 antisense polynucleotide whereby connexin 43 expression is downregulated over a sustained period of time. Conveniently, connexin 43 expression is downregulated for at least about 0.5 hours, about 1-2 hours, about 2-4 hours, about 4-6 hours, or about 6-8 hours, but may be administered for longer, e.g., up to 24 hours, or more. 0.5, 1-2 hour, and 4-8 hour sustained administrations are presently preferred. Suitable subjects include a diabetic subject. In other embodiments, the patient has a diabetic ulcer, a diabetic foot ulcer, a vasculitic ulcer, a venous ulcer, a venous stasis ulcer, an arterial ulcer, a pressure ulcer, a decubitus ulcer, an infectious ulcer, a trauma-induced ulcer, a burn ulcer, ulcerations associated with pyoderma gangrenosum, or a mixed ulcer or ulcers. Repeat applications are included within the invention. Preferred are repeat applications until wound closure is seen to be proceeding, followed by a repeat application (or applications) in the event wound healing once again becomes stalled or delayed.

According to a further aspect, sustained administration to the wound of an amount of a connexin 43 antisense polynucleotide effective to downregulate connexin 43 expression for a sustained period of time is provided. Further according to this aspect, wound healing of a wound that is not healing at expected rates is promoted, including delayed healing wounds, impaired healing wounds, and chonic wounds. In one embodiment the wound is a diabetic ulcer, a diabetic foot ulcer, a vasculitic ulcer, a venous ulcer, a venous stasis ulcer, an arterial ulcer, a pressure ulcer, a decubitus ulcer, an infectious ulcer, a trauma-induced ulcer, a burn ulcer, an ulceration associated with pyoderma gangrenosum, or a mixed ulcer or ulcers. Repeat applications are included within the invention. Preferred are repeat applications until wound closure is seen to be proceeding, followed by a repeat application (or applications) in the event wound healing once again becomes stalled or delayed.

According to other aspects of the present invention wound re-epithlialization and/or formation of granulation tissue is promoted.

In an additional aspect, the present invention provides a method of promoting wound healing in a subject having a wound that is not healing at an expected rate, including a delayed healing wound or an incomplete healing wound or a chronic wound, which comprises sustained administration of a connexin 43 antisense polynucleotide and a connexin 31.1 antisense polynucleotide. Repeat applications are included within the invention.

An alternative aspect of the present invention is directed to a method of promoting re-epithelialization of skin wounds which comprises administering to a subject having a wound that is not healing at the expected rate, including, for example, a delayed healing or an incompletely healing wound or a chronic wound, an anti-connexin polynucleotide, e.g., an anti-connexin polynucleotide in an amount effective to promote re-epithelialization. The anti-connexin polynucleotide may be targeted against a connexin selected from connexin 26, connexin 30, connexin 31.1 and connexin 43. Suitable polynucleotides may be selected from a modified or unmodified backbone connexin antisense polynucleotide (e.g., a DNA antisense polynucleotide that binds to a connexin mRNA), a RNAi polynucleotide and a siRNA polynucleotide. Repeat applications are included within the invention. Connexin 43 is presently a preferred target.

In an additional further aspect, the present invention provides a method of promoting wound healing in a subject having a wound that is not healing at the expected rate, including, for example, a delayed healing wound or an incomplete healing wound or a chronic wound, which comprises sustained administration of an anti-connexin polynucleotide, e.g., a connexin antisense polynucleotide, which is effective to regulate epithelial basal cell division and growth and an anti-connexin polynucleotide, e.g., a connexin antisense polynucleotide, which is effective to regulate outer layer keratin secretion. In one embodiment, the anti-connexin polynucleotide, e.g., connexin antisense polynucleotide, effective to regulate epithelial basal cell division or growth is a connexin 26 antisense polynucleotide or a connexin 43 antisense polynucleotide or a mixture thereof. According to an alternate embodiment, the anti-connexin polynucleotide, e.g., connexin antisense polynucleotide, is administered to regulate outer layer keratinization is a connexin 31.1 antisense polynucleotide. Repeat applications are included within the invention.

In another embodiment, the chronic wound is a chronic skin wound and an anti-connexin polynucleotide is administered to the skin or a tissue associated with the skin of said subject for an effective period of time. A chronic skin wound suitable for treatment may, for example, be selected from the group consisting of pressure ulcers, decubitus ulcers, diabetic ulcers, diabetic foot ulcers, venous ulcers, venous stasis ulcers, arterial ulcers, vasculitic ulcers, infectious ulcers, trauma-induced ulcers, burn ulcers, ulcerations associated with pyoderma gangrenosum, and mixed ulcers. The chronic wound may be an arterial ulcer which comprises ulcerations resulting from complete or partial arterial blockage. The chronic wound may be a venous ulcer or venous stasis ulcer which comprises ulcerations resulting from a malfunction of the venous valve and the associated vascular disease. The chronic wound may be a trauma-induced ulcer. Repeat applications are included within the invention.

According to another aspect, the present invention provides a method of increasing rate of wound healing or closure in a subject having a wound not healing at the expected rate (including a delayed-healing wound, an incompletely healing wound, and a chronic wound) which comprises administering to the subject an effective amount of an anti-connexin polynucleotide. A suitable polynucleotide is selected from a connexin antisense polynucleotide (e.g., a DNA antisense polynucleotide that binds to a connexin mRNA), a RNA polynucleotide and a siRNA polynucleotide. A suitable connexin antisense polynucleotide is a connexin 43 polynucleotide. Particularly suitable polynucleotides have from about 18 to about 32 nucleotides. Repeat applications are included within the invention. One presently preferred oligonucleotide is SEQ.ID.NO: 1.

The invention includes methods for the use of therapeutically effective amounts of one or more pharmaceutically acceptable anti-connexin polynucleotides, including connexin antisense polynucleotides, in the manufacture of a medicament or dosage form. Such medicaments, formulations and dosage forms include, for example, topical delivery forms and formulations. Such medicaments include those for the treatment of a subject as disclosed herein. Preferred anti-connexin polynucleotides and connexin antisense polynucleotides are anti-connexin 43 polynucleotides and connexin 43 antisense polynucleotides. Preferably, the medicament, formulation or dosage form is a foam, cream, spray or gel.

In another aspect, the invention includes an article of manufacture comprising a vessel containing a therapeutically effective amount of one or more pharmaceutically acceptable anti-connexin polynucleotides, e.g., connexin antisense polynucleotides, and instructions for use. Such instructions may include instructions regarding use for the treatment of a subject having a chronic wound or a wound characterized by delayed healing. Instructions may include instructions for use with regard to wounds that do not heal at expected rates, such as delayed healing wounds, incomplete healing wounds and chronic wounds. Preferred anti-connexin polynucleotides and connexin antisense polynucleotides are anti-connexin 43 polynucleotides and connexin 43 antisense polynucleotides.

The invention includes an article of manufacture comprising packaging material containing one or more dosage forms containing one or more pharmaceutically acceptable anti-connexin polynucleotides, e.g., connexin antisense polynucleotides, wherein the packaging material has a label that indicates that the dosage form can be used for a subject having or suspected of having or predisposed to any of the diseases, disorders and/or conditions described or referenced herein, including diseases, disorders and/or conditions characterized in whole or in part by impaired or delayed wound healing or a chronic wound, or other wounds that do not heal at expected rates. Such dosage forms include, for example, topical delivery forms and formulations. Preferred anti-connexin polynucleotides and connexin antisense polynucleotides are anti-connexin 43 polynucleotides and connexin 43 antisense polynucleotides.

In certain other aspect, the invention provides a package comprising an anti-connexin polynucleotide, e.g., a connexin antisense polynucleotide, together with instructions for use for the promotion (e.g., decrease in healing time, better wound outcome) of wound healing for a delayed or incompletely healing wound or a chronic wound.

In all aspects of the inventions, the anti-connexin polynucleotide is preferably a anti-connexin 43 polynucleotide, the connexin antisense polynucleotide is preferably a connexin 43 antisense polynucleotide, and the connexin antisense oligodeoxynucleotide is preferably a connexin 43 oligodeoxynucleotide.

These and other aspects of the present inventions, which are not limited to or by the information in this Brief Summary, are provided below.

BRIEF DESCRIPTION OF THE DRAWINGS

FIGS. 1A to 1D depict connexin immunostaining in the dermal fibroblasts, hair follicles, blood vessels and appendages. FIG. 1A depicts staining for connexin 43 in the epidermis and dermis and staining for connexin 26 in the epidermis in normal (open bars) and diabetic skin (solid bars), two weeks after induction of diabetes. The results are shown in graphical form, showing the number of plaques per area in normal (open bar) and diabetic (closed bar) epidermis or dermis. FIG. 1B depicts effects on connexin expression eight weeks after STZ induction of diabetes, by graphing number of plaques per area in normal (open bar) and diabetic (solid bar) skin. FIG. 1C depicts connextin immunostaining in control (C) and diabetic (D) at 8 weeks where arrowheads mark the boundary between epidermis and dermis. FIG. 1D depicts quantification of the distance of dye transfer of gap-junction permanent dye through tissue in five minutes in non-diabetic (open bars) and diabetic (solid bars) epidermis and dermis.

FIGS. 2A to 2D depict re-epithelialization rates and responses of connexin 43 and connexin 26 protein levels by measuring connexin staining after wounding. FIG. 2A depicts zones where connexin staining in keratinocytes was quantified: wound edge (WE), an adjacent zone 500 82 m away (AD) and leading edge (LE). Connexin staining at WE and AD were quantified one and two days after wounding. LE keratinocytes were imaged after 5 days. FIG. 2B depicts rate of re-epithelialization at 1, 2 and 5 days post wounding in control (C) and diabetic (D) skin. FIG. 2C graphically depicts connexin 43 staining (plaques per area) at 1, 2 and 5 days post wounding (first, second and third graph, respectively) in the WE, AD and LE in control (open bars) and diabetic (solid bars) animals. FIG. 2D graphically depicts connexin 26 staining (number of plaques per area) at 1, 2 and 5 days past wounding (first, second and third graph, respectively) in WE, AD and LE zones in control (open bars) and diabetic (solid bars) animals.

FIGS. 3*a*, 3*c* and 3*e* (control) and 3*a'*, 3*c'* and 3*e'* (diabetic) depict connexin 43 staining 1 (FIGS. 3*a* and 3*a'*), 2 (FIGS. 3*c* and 3*c'*) and 5 (FIGS. 3*e* and 3*e'*) days past wounding. FIGS. 3*b*, 3*d* and 3*f* (control) and 3*b'*, 3*d'* and 3*f'* (diabetic) depict connexin 26 staining 1 (FIGS. 3*b* and 3*b'*), 2 (FIGS. 3*d* and 3*d'*) and 5 (FIGS. 3*f* and 3*f*) after wounding.

FIGS. 4A (sense control) and FIG. 4B (connexin 43 antisense) depict connexin 43 expression in diabetic WE keratinocytes. FIG. 4C graphically depicts percent re-epithelialization, 1, 2 and 5 days post wounding in control (C) and diabetic (D) wounds with treatment with sense ("s") and connexin 43 antisense ("as") polynucleotides.

DETAILED DESCRIPTION

Figure 3A:
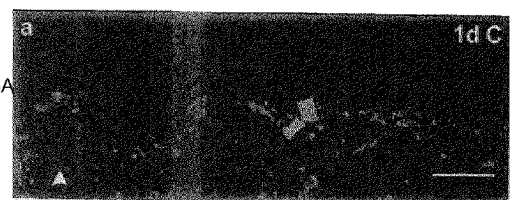
FIGS. 3*a* to 3*f* and 3*a'* to 3*f'* depict connexin staining 1, 2 and 5 days post wounding in control and diabetic animals.
Figure 3B:
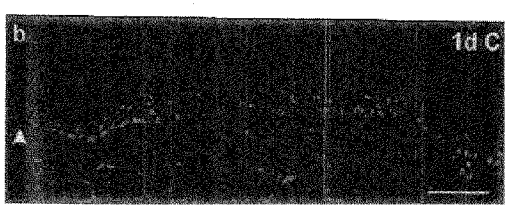
Figure 3A:
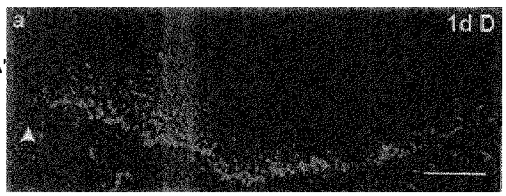
Figure 3B:
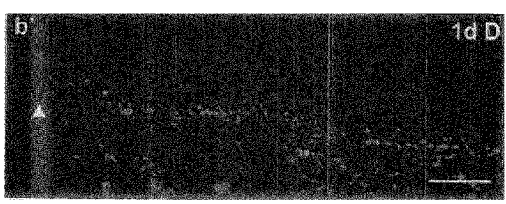

Wounds that do not heal at expected rates, including slow-healing wounds, delayed-healing wounds, incompletely healing wounds, dehiscent wounds, and chronic wounds often result in infection and can lead to amputation or death. Cell-cell communication through the gap junctions play pivotal roles in wound healing. It has been discovered that use of certain compounds, including those described or referenced herein, can block, inhibit, or alter cell communications, which promotes closure and healing in wounds that do not heal at expected rates, including slow-healing wounds, delayed-healing wounds, incompletely healing wounds, dehiscent wounds, and chronic wounds. For all applications, connexin 43 gap junction modulating agents are preferred.

Definitions

As used herein, a "disorder" is any disorder, disease, or condition that would benefit from an agent that promotes wound healing and/or reduces scar formation. For example, included are wound-associated abnormalities in connection with neuropathic, ischemic, and microvascular pathology; pressure over bony area [tailbone (sacral), hip (trochanteric), buttocks (ischial), or heel of the foot]; reperfusion injury; and conditions associated with valve reflux etiology and related conditions.

As used herein, "subject" refers to any mammal, including humans, domestic and farm animals, and zoo, sports, or pet animals, such as dogs, horses, cats, sheep, pigs, cows, etc. The preferred mammal herein is a human, including adults, children, and the elderly.

As used herein, "preventing" means preventing in whole or in part, or ameliorating or controlling.

As used herein, a "therapeutically effective amount" in reference to the compounds or compositions of the instant invention refers to the amount sufficient to induce a signs, symptoms, or causes of a disease or disorder or condition, or any other desired alteration of a biological system. In the present invention, the result will involve the promotion and/or improvement of wound healing, including rates of wound healing and closure of wounds, in whole or in part. Other benefits include decreases in swelling, inflammation and/or scar formation, in whole or in part.

As used herein, the term "treating" refers to both therapeutic treatment and prophylactic or preventative measures.

As used herein, "simultaneously" is used to mean that the one or more anti-connexin polynucleotides, e.g., antisense polynucleotides, are administered concurrently, whereas the term "in combination" is used to mean they are administered, if not simultaneously or in physical combination, then "sequentially" within a timeframe that they both are available to act therapeutically. Thus, administration "sequentially" may permit one agent to be administered within minutes (for example, 1, 2, 3, 4, 5, 10, 15, 20, 25, 30) minutes or a matter of hours, days, weeks or months after the other provided that one or more anti-connexin polynucleotides are concurrently present in effective amounts. The time delay between administration of the components will vary depending on the exact nature of the components, the interaction there between, and their respective half-lives.

As used herein, an "anti-connexin polynucleotide" decreases or inhibits expression of connexin mRNA and/or protein. Anti-connexin polynucleotides include, without limitation, antisense compounds such as antisense polynucleotides, other polynucleotides (such as polynucleotides having siRNA or ribozyme functions). Suitable examples of an anti-connexin polynucleotide include an antisense polynucleotide to a connexin. Accordingly, suitable anti-connexin polynucleotides include, for example, antisense polynucleotides (e.g., connexin 43 antisense polynucleotides) that modulate expression or activity of connexins and gap junctions in selected tissues, cells, and subjects.

The term "wound dressing" refers to a dressing for topical application to a wound and excludes compositions suitable for systemic administration. For example, the one or more anti-connexin polynucleotides, (such as connexin antisense polynucleotides) may be dispersed in or on a solid sheet of wound contacting material such as a woven or nonwoven textile material, or may be dispersed in a layer of foam such as polyurethane foam, or in a hydrogel such as a polyurethane hydrogel, a polyacrylate hydrogel, gelatin, carboxymethyl cellulose, pectin, alginate, and/or hyaluronic acid hydrogel, for example in a gel or ointment. In certain embodiments the one or more anti-connexin polynucleotides are dispersed in or on a biodegradable sheet material that provides sustained release of the active ingredients into the wound, for example a sheet of freeze-dried collagen, freeze-dried collagen/alginate mixtures (available under the Registered Trade Mark FIBRACOL from Johnson & Johnson Medical Limited) or freeze-dried collagen/oxidized regenerated cellulose (available under the Registered Trade Mark PROMOGRAN from Johnson & Johnson Medical Limited).

As used herein, "wound promoting matrix" includes for example, synthetic or naturally occurring matrices such as collagen, acellular matrix, crosslinked biological scaffold molecules, tissue based bioengineered structural framework, biomanufactured bioprostheses, and other implanted structures such as for example, vascular grafts suitable for cell infiltration and proliferation useful in the promotion of wound healing. Additional suitable biomatrix material may include chemically modified collagenous tissue to reduces antigenicity and immunogenicity. Other suitable examples include collagen sheets for wound dressings, antigen-free or antigen reduced acellular matrix (Wilson G J et al. (1990) Trans Am Soc Artif Intern 36:340-343) or other biomatrix which have been engineered to reduce the antigenic response to the xenograft material. Other matrices useful in promotion of wound healing may include for example, processed bovine pericardium proteins comprising insoluble collagen and elastin (Courtman D W et al. (1994) J Biomed Mater Res 28:655-666) and other acellular tissue which may be useful for providing a natural microenvironment for host cell migration to accelerate tissue regeneration (Malone J M et al. (1984) J Vasc Surg 1:181-91). The invention contemplates a synthetic or natural matrix comprising one or more anti-connexin polypeptides described herein, including anti-connexin 43 polypeptides. Connexin 43 antisense oligodeoxynucleotides are preferred.

As used herein, the term "wound" includes an injury to any tissue, including for example, delayed or difficult to heal wounds, and chronic wounds. Examples of wounds may include both open and closed wounds. The term "wound" may also include for example, injuries to the skin and subcutaneous tissue initiated in different ways (e.g., pressure sores from extended bed rest and wounds induced by trauma) and with varying characteristics. Wounds may be classified into one of four grades depending on the depth of the wound: i) Grade I wounds limited to the epithelium; ii) Grade II wounds extending into the dermis; iii) Grade III wounds extending into the subcutaneous tissue; and iv) Grade IV (or full-thickness wounds) wounds wherein bones are exposed (e.g., a bony pressure point such as the greater trochanter or the sacrum).

The term "partial thickness wound" refers to wounds that encompass Grades I-III. Examples of partial thickness wounds include pressure sores, venous stasis ulcers, and diabetic ulcers. The present invention contemplates treating all wounds of a type that do not heal at expected rates, including, delayed-healing wounds, incompletely healing wounds, and chronic wounds.

"Wound that does not heal at the/an expected rate" means an injury to any tissue, including delayed or difficult to heal wounds (including delayed or incompletely healing wounds), and chronic wounds. Examples of wounds that do not heal at the expected rate include ulcers, such as diabetic ulcers, diabetic foot ulcers, vascultic ulcers, arterial ulcers, venous ulcers, venous stasis ulcers, pressure ulcers, decubitus ulcers, infectious ulcers, trauma-induced ulcers, burn ulcers, ulcerations associated with pyoderma gangrenosum, and mixed ulcers. Other wounds that do not heal at expected rates include dehiscent wounds As used herein, a delayed or difficult to heal wound may include, for example, a wound that is characterized at least in part by 1) a prolonged inflammatory phase, 2) a slow forming extracellular matrix, and/or 3) a decreased rate of epithelialization or closure.

The term "chronic wound" generally refers to a Wound that has not healed. Wounds that do not heal within three months, for example, are considered chronic. Chronic wounds include venous ulcers, venous stasis ulcers, arterial ulcers, pressure ulcers, diabetic ulcers, diabetic foot ulcers, vasculitic ulcers, decubitus ulcers, burn ulcers, trauma-induced ulcers, infectious ulcers, mixed ulcers, and pyoderma gangrenosum. The chronic wound may be an arterial ulcer which comprises ulcerations resulting from complete or partial arterial blockage. The chronic wound may be a venous or venous stasis ulcer which comprises ulcerations resulting from a malfunction of the venous valve and the associated vascular disease. In certain embodiments a method of treating a chronic wound is provided where the chronic wound is characterized by one or more of the following AHCPR stages of pressure ulceration: stage 1, stage 2, stage 3, and/or stage 4.

As used herein, chronic wound may refer to, for example, a wound that is characterized at least in part by one or more of (1) a chronic self-perpetuating state of wound inflammation, (2) a deficient and defective wound extracellular matrix, (3) poorly responding (senescent) wound cells especially fibroblasts, limiting extracellular matrix production, and/or (4) failure of re-epithelialization due in part to lack of the necessary extracellular matrixorchestration and lack of scaffold for migration. Chronic wounds may also be characterized by 1) prolonged inflammation and proteolytic activity leading to ulcerative lesions, including for example, diabetic, pressure (decubitous), venous, and arterial ulcers; 2) progressive deposition of matrix in the affected area, 3) longer repair times, 4) less wound contraction, 5) slower re-epithelialization, and 6) increased thickness of granulation tissue.

Exemplary chronic wounds may include "pressure ulcers." Exemplary pressure ulcers may be classified into 4 stages based on AHCPR (Agency for Health Care Policy and Research, U.S. Department of Health and Human Services) guidelines. A stage I pressure ulcer is an observable pressure related alteration of intact skin whose indicators as compared to the adjacent or opposite area on the body may include changes in one or more of the following: skin temperature (warmth or coolness), tissue consistency (firm or boggy feel) and/or sensation (pain, itching). The ulcer appears as a defined area of persistent redness in lightly pigmented skin, whereas in darker skin tones, the ulcer may appear with persistent red, blue, or purple hues. Stage 1 ulceration may include nonblanchable erythema of intact skin and the heralding lesion of skin ulceration. In individuals with darker skin, discoloration of the skin, warmth, edema, induration, or hardness may also be indicators of stage 1 ulceration. Stage 2 ulceration may be characterized by partial thickness skin loss involving epidermis, dermis, or both. The ulcer is superficial and presents clinically as an abrasion, blister, or shallow crater. Stage 3 ulceration may be characterized by full thickness skin loss involving damage to or necrosis of subcutaneous tissue that may extend down to, but not through, underlying fascia. The ulcer presents clinically as a deep crater with or without undermining of adjacent tissue. Stage 4 ulceration may be characterized by full thickness skin loss with extensive destruction, tissue necrosis, or damage to muscle, bone, or supporting structures (e.g., tendon, joint capsule). In certain embodiments a method of treating a chronic wound is provided where the chronic wound is characterized by one or more of the following AHCPR stages of pressure ulceration: stage 1, stage 2, stage 3, and/or stage 4.

Exemplary chronic wounds may also include "decubitus ulcers." Exemplary decubitus ulcers may arise as a result of prolonged and unrelieved pressure over a bony prominence that leads to ischemia. The wound tends to occur in patients who are unable to reposition themselves to off-load weight, such as paralyzed, unconscious, or severely debilitated persons. As defined by the U.S. Department of Health and Human Services, the major preventive measures include identification of high-risk patients; frequent assessment; and prophylactic measures such as scheduled repositioning, appropriate pressure-relief bedding, moisture barriers, and adequate nutritional status. Treatment options may include for example, pressure relief, surgical and enzymatic debridement, moist wound care, and control of the bacterial load. In certain embodiments a method of treating a chronic wound is provided wherein the chronic wound is characterized by decubitus ulcer or ulceration, which results from prolonged, unrelieved pressure over a bony prominence that leads to ischemia.

Chronic wounds may also include "arterial ulcers." Chronic arterial ulcers are generally understood to be ulcerations that accompany arteriosclerotic and hypertensive cardiovascular disease. They are painful, sharply marginated, and often found on the lateral lower extremities and toes. Arterial ulcers may be characterized by complete or partial arterial blockage, which may lead to tissue necrosis and/or ulceration. Signs of arterial ulcer may include, for example, pulselessness of the extremity; painful ulceration; small, punctate ulcers that are usually well circumscribed; cool or cold skin; delayed capillary return time (briefly push on the end of the toe and release, normal color should return to the toe in about 3 seconds or less); atrophic appearing skin (for example, shiny, thin, dry); and loss of digital and pedal hair. In certain embodiments a method of treating a chronic wound is provided wherein the chronic wound is characterized by arterial ulcers or ulcerations due to complete or partial arterial blockage.

Exemplary chronic wounds may include "venous ulcers." Exemplary venous ulcers are the most common type of ulcer affecting the lower extremities and may be characterized by malfunction of the venous valve. The normal vein has valves that prevent the backflow of blood. When these valves become incompetent, the backflow of venous blood causes venous congestion. Hemoglobin from the red blood cells escapes and leaks into the extravascular space, causing the brownish discoloration commonly noted. It has been shown that the transcutaneous oxygen pressure of the skin surrounding a venous ulcer is decreased, suggesting that there are forces obstructing the normal vascularity of the area. Lymphatic drainage and flow also plays a role in these ulcers. The venous ulcer may appear near the medial malleolus and usually occurs in combination with an edematous and indurated lower extremity; it may be shallow, not too painful and may present with a weeping discharge from the affected site. In certain embodiments a method of treating a chronic wound is provided wherein the chronic wound is characterized by venous ulcers or ulcerations due to malfunction of the venous valve and the associated vascular disease. In certain embodiments a method of treating a chronic wound is provided wherein the chronic wound is characterized by arterial ulcers or ulcerations due to complete or partial arterial blockage.

Exemplary chronic wounds may include "venous stasis ulcers." Stasis ulcers are lesions associated with venous insufficiency are more commonly present over the medial malleolus, usually with pitting edema, varicosities, mottled pigmentation, erythema, and nonpalpable petechiae and purpura. The stasis dermatitis and ulcers are generally pruritic rather than painful. Exemplary venous stasis ulcers may be characterized by chronic passive venous congestion of the lower extremities results in local hypoxia. One possible mechanism of pathogenesis of these wounds includes the impediment of oxygen diffusion into the tissue across thick perivascular fibrin cuffs. Another mechanism is that macromolecules leaking into the perivascular tissue trap growth factors needed for the maintenance of skin integrity. Additionally, the flow of large white blood cells slows due to venous congestion, occluding capillaries, becoming activated, and damaging the vascular endothelium to predispose to ulcer formation. In certain embodiments a method of treating a chronic wound is provided wherein the chronic wound is characterized by venous ulcers or ulcerations due to malfunction of the venous valve and the associated vascular disease. In certain embodiments a method of treating a chronic wound is provided wherein the chronic wound is characterized by venous stasis ulcers or ulcerations due to chronic passive venous congestion of the lower extremities and/or the resulting local hypoxia.

Exemplary chronic wounds may include "diabetic ulcers." Diabetic patients are prone to ulcerations, including foot ulcerations, due to both neurologic and vascular complications. Peripheral neuropathy can cause altered or complete loss of sensation in the foot and/or leg. Diabetic patients with advanced neuropathy loose all ability for sharp-dull discrimination. Any cuts or trauma to the foot may go completely unnoticed for days or weeks in a patient with neuropathy. It is not uncommon to have a patient with neuropathy notice that the ulcer "just appeared" when, in fact, the ulcer has been present for quite some time. For patients of neuropathy, strict glucose control has been shown to slow the progression of the disease. Charcot foot deformity may also occur as a result of decreased sensation. People with "normal" feeling in their feet have the ability to sense automatically when too much pressure is being placed on an area of the foot. Once identified, our bodies instinctively shift position to relieve this stress. A patient with advanced neuropathy looses this ability to sense the sustained pressure insult, as a result, tissue ischemia and necrosis may occur leading to for example, plantar ulcerations. Additionally, microfractures in the bones of the foot, if unnoticed and untreated, may result in disfigurement, chronic swelling and additional bony prominences. Microvascular disease is one of the significant complications for diabetics, which may also lead, to ulcerations. In certain embodiments a method of treating a chronic wound is provided wherein the chronic wound is characterized by diabetic foot ulcers and/or ulcerations due to both neurologic and vascular complications of diabetes.

Exemplary chronic wounds can include "traumatic ulcers." Formation of traumatic ulcers may occur as a result of traumatic injuries to the body. These injuries include, for example, compromises to the arterial, venous or lymphatic systems; changes to the bony architecture of the skeleton; loss of tissue layers-epidermis, dermis, subcutaneous soft tissue, muscle or bone; damage to body parts or organs and loss of body parts or organs. In certain embodiments, a method of treating a chronic wound is provided wherein the chronic wound is characterized by ulcerations associated with traumatic injuries to the body.

Exemplary chronic wounds can include "burn ulcers", including 1st degree burn (i.e. superficial, reddened area of skin); 2nd degree burn (a blistered injury site which may heal spontaneously after the blister fluid has bee removed); 3rd degree burn (burn through the entire skin and usually require surgical intervention for wound healing); scalding (may occur from scalding hot water, grease or radiator fluid); thermal (may occur from flames, usually deep burns); chemical (may come from acid and alkali, usually deep burns); electrical (either low voltage around a house or high voltage at work); explosion flash (usually superficial injuries); and contact burns (usually deep and may occur from muffler tail pipes, hot irons and stoves). In certain embodiments, a method of treating a chronic wound is provided wherein the chronic wound is characterized by ulcerations associated with burn injuries to the body.

Exemplary chronic wounds can include "vasculitic ulcers." Vasculitic ulcers also occur on the lower extremities and are painful, sharply marginated lesions, which may have associated palpable purpuras and hemorrhagic bullae. The collagen diseases, septicemias, and a variety of hematological disorders (e.g., thrombocytopenia, dysproteinemia) may be the cause of this severe, acute condition.

Exemplary chronic wounds can include pyoderma gangrenosum. Pyoderma gangrenosum occurs as single or multiple, very tender ulcers of the lower legs. A deep red to purple, undermined border surrounds the purulent central defect. Biopsy typically fails to reveal a vasculitis. In half the patients it is associated with a systemic disease such as ulcerative colitis, regional ileitis, or leukemia. In certain embodiments, a method of treating a chronic wound is provided wherein the chronic wound is characterized by ulcerations associated with pyoderma gangrenosum.

Exemplary chronic wounds can include infectious ulcers. Infectious ulcers follow direct innoculation with a variety of organisms and may be associated with significant regional adenopathy. Mycobacteria infection, anthrax, diphtheria, blastomyosis, sporotrichosis, tularemia, and cat-scratch fever are examples. The genital ulcers of primary syphilis are typically nontender with a clean, firm base. Those of chancroid and granuloma inguinale tend to be ragged, dirty, and more extravagant lesions. In certain embodiments, a method of treating a chronic wound is provided wherein the chronic wound is characterized by ulcerations associated with infection.

As used herein, the term "dehiscent wound" refers to a wound, usually a surgical wound, which has ruptured or split open. In certain embodiments, a method of treating a wound that does not heal at the expected rate is provided wherein the wound is characterized by dehiscence.

Anti-connexin Polynucleotides

Anti-connexin polynucleotides include connexin antisense polynucleotides as well as polynucleotides which have functionalities which enable them to downregulate connexin expression (for example, by downregulation of mRNA transcription or translation). In the case of downregulation, this will have the effect of reducing direct cell-cell communication by gap junctions at the site at which connexin expression is downregulated.

Suitable anti-connexin polynucleotides include RNAi polynucleotides and siRNA polynucleotides.

Synthesis of antisense polynucleotides and other anti-connexin polynucleotides such as RNAi, siRNA, and ribozyme polynucleotides as well as polynucleotides having modified and mixed backbones is known to those of skill in the art. See e.g. Stein C. A. and Krieg A. M. (eds), Applied Antisense Oligonucleotide Technology, 1998 (Wiley-Liss).

According to one aspect, the downregulation of connexin expression may be based generally upon the antisense approach using antisense polynucleotides (such as DNA or RNA polynucleotides), and more particularly upon the use of antisense oligodeoxynucleotides (ODN). These polynucleotides (e.g., ODN) target the connexin protein (s) to be downregulated. Typically the polynucleotides are single stranded, but may be double stranded.

The antisense polynucleotide may inhibit transcription and/or translation of a connexin. Preferably the polynucleotide is a specific inhibitor of transcription and/or translation from the connexin gene or mRNA, and does not inhibit transcription and/or translation from other genes or mRNAs. The product may bind to the connexin gene or mRNA either (i) 5' to the coding sequence, and/or (ii) to the coding sequence, and/or (iii) 3' to the coding sequence.

The antisense polynucleotide is generally antisense to a connexin mRNA. Such a polynucleotide may be capable of hybridizing to the connexin mRNA and may thus inhibit the expression of connexin by interfering with one or more aspects of connexin mRNA metabolism including transcription, mRNA processing, mRNA transport from the nucleus, translation or mRNA degradation. The antisense polynucleotide typically hybridizes to the connexin mRNA to form a duplex which can cause direct inhibition of translation and/or destabilization of the mRNA. Such a duplex may be susceptible to degradation by nucleases.

The antisense polynucleotide may hybridize to all or part of the connexin mRNA. Typically the antisense polynucleotide hybridizes to the ribosome binding region or the coding region of the connexin mRNA. The polynucleotide may be complementary to all of or a region of the connexin mRNA. For example, the polynucleotide may be the exact complement of all or a part of connexin mRNA. However, absolute complementarity is not required and polynucleotides which have sufficient complementarity to form a duplex having a melting temperature of greater than about 20° C., 30° C. or 40° C. under physiological conditions are particularly suitable for use in the present invention.

Thus the polynucleotide is typically a homologue of a sequence complementary to the mRNA. The polynucleotide may be a polynucleotide which hybridizes to the connexin mRNA under conditions of medium to high stringency such as 0.03M sodium chloride and 0.03M sodium citrate at from about 50° C. to about 60° C.

For certain aspects, suitable polynucleotides are typically from about 6 to 40 nucleotides in length. Preferably a polynucleotide may be from about 12 to about 35 nucleotides in length, or alternatively from about 12 to about 20 nucleotides in length or more preferably from about 18 to about 32 nucleotides in length. According to an alternative aspect, the polynucleotide may be at least about 40, for example at least about 60 or at least about 80, nucleotides in length and up to about 100, about 200, about 300, about 400, about 500, about 1000, about 2000 or about 3000 or more nucleotides in length.

The connexin protein or proteins targeted by the polynucleotide will be dependent upon the site at which downregulation is to be effected. This reflects the non-uniform make-up of gap junction(s) at different sites throughout the body in terms of connexin sub-unit composition. The connexin is a connexin that naturally occurs in a human or animal in one aspect or naturally occurs in the tissue in which connexin expression or activity is to be decreased.

The connexin gene (including coding sequence) generally has homology with the coding sequence of one or more of the specific connexins mentioned herein, such as homology with the connexin 43 coding sequence shown in Table 2. The connexin is typically an α or β connexin. Preferably the connexin is an a connexin and is expressed in the tissue to be treated.

Some connexin proteins are however more ubiquitous than others in terms of distribution in tissue. One of the most widespread is connexin 43. Polynucleotides targeted to connexin 43 are particularly suitable for use in the present invention. In other aspects other connexins are targeted.

In one preferred aspect, the antisense polynucleotides are targeted to the mRNA of one connexin protein only. Most preferably, this connexin protein is connexin 43. In another aspect, connexin protein is connexin 26, 30, 31.1, 32, 36, 37, 40, or 45. In other aspects, the connexin protein is connexin 30.3, 31, 40.1, or 46.6.

It is also contemplated that polynucleotides targeted to separate connexin proteins be used in combination (for example 1, 2, 3, 4 or more different connexins may be targeted). For example, polynucleotides targeted to connexin 43, and one or more other members of the connexin family (such as connexin 26, 30, 30.3, 31.1, 32, 36, 37, 40, 40.1, 45, and 46.6) can be used in combination.

Alternatively, the antisense polynucleotides may be part of compositions which may comprise polynucleotides to more than one connexin protein. Preferably, one of the connexin proteins to which polynucleotides are directed is nucleotides may vary in length. A 30 mer polynucleotide has been found to be particularly suitable.

Many aspects of the invention are described with reference to oligodeoxynucleotides. However it is understood that other suitable polynucleotides (such as RNA polynucleotides) may be used in these aspects.

The antisense polynucleotides may be chemically modified. This may enhance their resistance to nucleases and may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. Alternatively mixed backbone oligonucleotides ("MBOs") may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides. Methods of preparing modified backbone and mixed backbone oligonucleotides are known in the art.

The precise sequence of the antisense polynucleotide used in the invention will depend upon the target connexin protein. In one embodiment, suitable connexin antisense polynucleotides can include polynucleotides such as oligodeoxynucleotides selected from the following sequences set forth in Table 1:

TABLE 1

| | | |
|---|---|---|
| 5' GTA ATT GCG GCA AGA AGA ATT GTT TCT GTC 3'(connexin 43) | (SEQ. ID. NO: 1) |
| 5' GTA ATT GCG GCA GGA GGA ATT GTT TCT GTC 3'(connexin 43) | (SEQ. ID. NO: 2) |
| 5' GGC AAG AGA CAC CAA AGA CAC TAC CAG CAT 3'(connexin 43) | (SEQ. ID. NO: 3) |
| 5' TCC TGA GCA ATA CCT AAC GAA CAA ATA 3' | (connexin 26) | (SEQ. ID. NO: 4) |
| 5' CAT CTC CTT GGT GCT CAA CC 3' | (connexin 37) | (SEQ. ID. NO: 5) |
| 5' CTG AAG TCG ACT TGG CTT GG 3' | (connexin 37) | (SEQ. ID. NO: 6) |
| 5' CTC AGA TAG TGG CCA GAA TGC 3' | (connexin 30) | (SEQ. ID. NO: 7) |
| 5' TTG TCC AGG TGA CTC CAA GG 3' | (connexin 30) | (SEQ. ID. NO: 8) |
| 5' CGT CCG AGC CCA GAA AGA TGA GGT C 3' | (connexin 31.1) | (SEQ. ID. NO: 9) |
| 5' AGA GGC GCA CGT GAG ACA C 3' | (connexin 31.1) | (SEQ .ID. NO: 10) |
| 5' TGA AGA CAA TGA AGA TGT T 3' | (connexin 31.1) | (SEQ. ID. NO: 11) |
| 5' TTT CTT TTC TAT GTG CTG TTG GTG A 3' | (connexin 32) | (SEQ. ID. NO: 12) | connexin 43. Other connexin proteins to which oligodeoxynucleotides are directed may include, for example, connexins 26, 30, 30.3, 31.1, 32, 36, 37, 40, 40.1, 45, and 46.6. Suitable exemplary polynucleotides (and ODNs) directed to various connexins are set forth in Table 1.

Individual antisense polynucleotides may be specific to a particular connexin, or may target 1, 2, 3 or more different connexins. Specific polynucleotides will generally target sequences in the connexin gene or mRNA which are not conserved between connexins, whereas non-specific polynucleotides will target conserved sequences for various connexins.

The polynucleotides for use in the invention may suitably be unmodified phosphodiester oligomers. Such oligodeoxy- Suitable polynucleotides for the preparation of the combined polynucleotide compositions described herein include for example, polynucleotides to connexin 43 and polynucleotides for connexins 26, 30, 31.1, 32 and 37 as described in Table 1 above.

Although the precise sequence of the antisense polynucleotide used in the invention will depend upon the target connexin protein, for connexin 43, antisense polynucleotides having the following sequences have been found to be particularly suitable:

(SEQ. ID. NO: 1)
GTA ATT GCG GCA AGA AGA ATT GTT TCT GTC;

```
                                           (SEQ. ID. NO: 2)
GTA ATT GCG GCA GGA GGA ATT GTT TCT GTC;
and (SEQ. ID. NO: 3)
GGC AAG AGA CAC CAA AGA CAC TAC CAG CAT.
```

For example, suitable antisense polynucleotides for connexins 26, 31.1 and 32 have the following sequences:

```
                                           (SEQ. ID. NO: 4)
5' TCC TGA GCA ATA CCT AAC GAA CAA ATA
(connexin 26);

(SEQ. ID. NO: 9)
5' CGT CCG AGC CCA GAA AGA TGA GGT C 3
(connexin 31.1);
and (SEQ. ID. NO: 12)
5' TTT CTT TTC TAT GTG CTG TTG GTG A
(connexin 32).
```

Other connexin antisense polynucleotide sequences useful according to the methods of the present invention include:

```
                                           (SEQ. ID. NO: 5)
5' CAT CTC CTT GGT GCT CAA CC 3' (connexin 37);

(SEQ. ID. NO: 6)
5' CTG AAG TCG ACT TGG CTT GG 3' (connexin 37);

(SEQ. ID. NO: 7)
5' CTC AGA TAG TGG CCA GAA TGC 3' (connexin 30);

(SEQ. ID. NO: 8)
5' TTG TCC AGG TGA CTC CAA GG 3' (connexin 30);

(SEQ. ID. NO: 10)
5' AGA GGC GCA CGT GAG ACA C 3' (connexin 31.1);
and (SEQ. ID. NO: 11)
5' TGA AGA CAA TGA AGA TGT T 3' (connexin 31.1).
```

Polynucleotides, including ODN's, directed to connexin proteins can be selected in terms of their nucleotide sequence by any convenient, and conventional, approach. For example, the computer programs MacVector and OligoTech (from Oligos etc. Eugene, Oreg., USA) can be used. Once selected, the ODN's can be synthesized using a DNA synthesizer.

Polynucleotide Homologues

Homology and homologues are discussed herein (for example, the polynucleotide may be a homologue of a complement to a sequence in connexin mRNA). Such a polynucleotide typically has at least about 70% homology, preferably at least about 80%, at least about 90%, at least about 95%, at least about 97% or at least about 99% homology with the relevant sequence, for example over a region of at least about 15, at least about 20, at least about 40, at least about 100 more contiguous nucleotides (of the homologous sequence).

Homology may be calculated based on any method in the art. For example the UWGCG Package provides the BESTFIT program, which can be used to calculate homology (for example used on its default settings) (Devereux et al. (1984) Nucleic Acids Research 12, p387-395). The PILEUP and BLAST algorithms can be used to calculate homology or line up sequences (typically on their default settings), for example as described in Altschul S. F. (1993) J Mol Evol 36: 290-300; Altschul, S, F et al (1990) J Mol Biol 215: 403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached.

The BLAST algorithm parameters W, T and X determine the sensitivity and speed of the alignment. The BLAST program uses as defaults a word length (W), the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to a second sequence is less than about 1, preferably less than about 0.1, more preferably less than about 0.01, and most preferably less than about 0.001.

The homologous sequence typically differs from the relevant sequence by at least about (or by no more than about) 2, 5, 10, 15, 20 more mutations (which may be substitutions, deletions or insertions). These mutations may be measured across any of the regions mentioned above in relation to calculating homology.

The homologous sequence typically hybridizes selectively to the original sequence at a level significantly above background. Selective hybridization is typically achieved using conditions of medium to high stringency (for example 0.03M sodium chloride and 0.03M sodium citrate at from about 50° C. to about 60° C.). However, such hybridization may be carried out under any suitable conditions known in the art (see Sambrook et al. (1989), Molecular Cloning: A Laboratory Manual). For example, if high stringency is required, suitable conditions include 0.2×SSC at 60° C. If lower stringency is required, suitable conditions include 2×SSC at 60° C.

Dosage Forms and Formulations and Administration

The agents of the invention of the may be administered to a subject in need of treatment, such as a subject with any of the wounds mentioned herein. The condition of the subject can thus be improved. The anti-connexin polynucleotide may be used in the treatment of the subject's body by therapy. They may be used in the manufacture of a medicament to treat any of the wounds mentioned herein.

The anti-connexin polynucleotide may be present in a substantially isolated form. It will be understood that the product may be mixed with carriers or diluents which will not interfere with the intended purpose of the product and still be regarded as substantially isolated. A product of the invention may also be in a substantially purified form, in which case it will generally comprise about 80%, 85%, or 90%, including, for example, at least about 95%, at least about 98% or at least about 99% of the polynucleotide or dry mass of the preparation.

Depending on the intended route of administration, the pharmaceutical products, pharmaceutical compositions, combined preparations and medicaments of the invention may, for example, take the form of solutions, suspensions, instillations, sprays, salves, creams, gels, foams, ointments, emulsions, lotions, paints, sustained release formulations, or powders, and typically contain about 0.01% to about 1% of active ingredient(s), about 1%-50% or active ingredient(s), about 2%-60% of active ingredient(s), about 2%-70% of active ingredient(s), or up to about 90%) of active ingredient(s). Other suitable formulations include pluronic gel-based formulations, carboxymethylcellulose (CMC)-based formulations, and hyroxypropylmethylcellulose (HPMC)-based formulations. Other useful formulations include slow or delayed release preparations.

Gels or jellies may be produced using a suitable gelling agent including, but not limited to, gelatin, tragacanth, or a cellulose derivative and may include glycerol as a humectant, emollient, and preservative. Ointments are semi-solid preparations that consist of the active ingredient incorporated into a fatty, waxy, or synthetic base. Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Preferably the agents of the invention are combined with a pharmaceutically acceptable carrier or diluent to produce a pharmaceutical composition. Suitable carriers and diluents include isotonic saline solutions, for example phosphate-buffered saline. Suitable diluents and excipients also include, for example, water, saline, dextrose, glycerol, or the like, and combinations thereof. In addition, if desired substances such as wetting or emulsifying agents, stabilizing or ph buffering agents may also be present.

The term "pharmaceutically acceptable carrier" refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, and amino acid copolymers.

Pharmaceutically acceptable salts can also be present, e.g., mineral acid salts such as hydrochlorides, hydrobromides, phosphates, sulfates, and the like; and the salts of organic acids such as acetates, propionates, malonates, benzoates, and the like.

Suitable carrier materials include any carrier or vehicle commonly used as a base for creams, lotions, sprays, foams, gels, emulsions, lotions or paints for topical administration. Examples include emulsifying agents, inert carriers including hydrocarbon bases, emulsifying bases, non-toxic solvents or water-soluble bases. Particularly suitable examples include pluronics, HPMC, CMC and other cellulose-based ingredients, lanolin, hard paraffin, liquid paraffin, soft yellow paraffin or soft white paraffin, white beeswax, yellow beeswax, cetostearyl alcohol, cetyl alcohol, dimethicones, emulsifying waxes, isopropyl myristate, microcrystalline wax, oleyl alcohol and stearyl alcohol.

Preferably, the pharmaceutically acceptable carrier or vehicle is a gel, suitably a nonionic polyoxyethylene-polyoxypropylene copolymer gel, for example, a Pluronic gel, preferably Pluronic F-127 (BASF Corp.). This gel is particularly preferred as it is a liquid at low temperatures but rapidly sets at physiological temperatures, which confines the release of the agent to the site of application or immediately adjacent that site.

An auxiliary agent such as casein, gelatin, albumin, glue, sodium alginate, carboxymethylcellulose, methylcellulose, hydroxyethylcellulose or polyvinyl alcohol may also be included in the formulation of the invention.

Other suitable formulations include pluronic gel-based formulations, carboxymethylcellulose (CMC)-based formulations, and hydroxypropylmethylcellulose (HPMC)-based formulations. The composition may be formulated for any desired form of delivery, including topical, instillation, parenteral, intramuscular, subcutaneous, or transdermal administration. Other useful formulations include slow or delayed release preparations.

The formulation which is administered may contain transfection agents. Examples of such agents include cationic agents (for example calcium phosphate and DEAE-dextran) and lipofectants (for example Lipofectam™ and Transfectam™), and surfactants.

In one embodiment, the formulation further includes a surfactant to assist with polynucleotide cell penetration or the formulation may contain any suitable loading agent. Any suitable non-toxic surfactant may be included, such as DMSO. Alternatively a transdermal penetration agent such as urea may be included.

The effective dose for a given subject preferably lies within the dose that is therapeutically effective for at least 50% of the population, and that exhibits little or no toxicity at this level.

The effective dosage of each of the anti-connexin polynucleotides employed in the methods and compositions of the invention may vary depending on a number of factors including the particular anti-connexin polynucleotide employed, the mode of administration, the frequency of administration, the wound being treated, the severity of the wound being treated, the route of administration, the needs of a patient sub-population to be treated or the needs of the individual patient which different needs can be due to age, sex, body weight, relevant medical wound specific to the patient.

A suitable dose may be from about 0.001 to about 1 mg/kg body weight such as about 0.01 to about 0.4 mg/kg body weight. A suitable dose may however be from about 0.001 to about 0.1 mg/kg body weight such as about 0.01 to about 0.050 mg/kg body weight. Doses from about 1 to 100, 200, 300, 400, and 500 micrograms are appropriate. As noted herein, repeat applications are contemplated. Repeat applications are typically applied about once per week, or when wound-healing may appear to be stalled or slowing.

Still other dosage levels between about 1 nanogram (ng)/kg and about 1 mg/kg body weight per day of each of the agents described herein. In certain embodiments, the dosage of each of the subject compounds will generally be in the range of about 1 ng to about 1 microgram per kg body weight, about 1 ng to about 0.1 microgram per kg body weight, about 1 ng to about 10 ng per kg body weight, about 10 ng to about 0.1 microgram per kg body weight, about 0.1 microgram to about 1 microgram per kg body weight, about 20 ng to about 100 ng per kg body weight, about 0.001 mg to about 100 mg per kg body weight, about 0.01 mg to about 10 mg per kg body weight, or about 0.1 mg to about 1 mg per kg body weight. In certain embodiments, the dosage of each of the subject compounds will generally be in the range of about 0.001 mg to about 0.01 mg per kg body weight, about 0.01 mg to about 0.1 mg per kg body weight, about 0.1 mg to about 1 mg per kg body weight, or about 1 mg per kg body weight. If more than one anti-connexin polynucleotide is used, the dosage of each anti-connexin polynucleotide need not be in the same range as the other. For example, the dosage of one anti-connexin polynucleotide may be between about 0.01 mg to about 1 mg per kg body weight, and the dosage of another anti-connexin polynucleotide may be between about 0.1 mg to about 1 mg per kg body weight. As noted herein, repeat applications are contemplated. Repeat applications are typically applied about once per week, or when wound-healing may appear to be stalled or slowing.

Other useful doses range from about 1 to about 10 micrograms per square centimeter of wound size. Certain doses will be about 1-2, about 1-5, about 2-4, about 5-7, and about 8-10 micrograms per square centimeter of wound size. Other useful doses are greater than about 10 micrograms per square centimeter of wound size, including about 15 micrograms per square centimeter of wound size, about 20 micrograms per square centimeter of wound size, about 25 micrograms per square centimeter of wound size, about 30 micrograms per square centimeter of wound size, about 35 micrograms per square centimeter of wound size, about 40 micrograms per square centimeter of wound size, about 50 micrograms per square centimeter of wound size, and about 100 micrograms per square centimeter of wound size. Other useful doses are about 150 micrograms per square centimeter of wound size, about 200 micrograms per square centimeter of wound size, about 250 micrograms per square centimeter of wound size, or about 500 micrograms per square centimeter of wound size. As noted herein, repeat applications are contemplated. Repeat applications are typically applied about once per week, or when wound-healing may appear to be stalled or slowing.

For example, in certain embodiments, the anti-connexin polynucleotide composition may be applied at about 0.01 micromolar ($\mu$M) or 0.05 $\mu$M to about 200 $\mu$M final concentration at the treatment site and/or adjacent to the treatment site. Preferably, the antisense polynucleotide composition is applied at about 0.05 $\mu$M to about 100 $\mu$M final concentration, more preferably, the anti-connexin polynucleotide composition is applied at about 1.0 $\mu$M to about 50 $\mu$M final concentration, and more preferably, the anti-connexin polynucleotide composition is applied at about 5-10 $\mu$M to about 30-50 $\mu$M final concentration. Additionally, the anti-connexin polynucleotide composition is applied at about 8 $\mu$M to about 20 $\mu$M final concentration, and alternatively the anti-connexin polynucleotide composition is applied at about 10 $\mu$M to about 20 $\mu$M final concentration, or at about 10 to about 15 $\mu$M final concentration. In certain other embodiments, the anti-connexin polynucleotide is applied at about 10 $\mu$M final concentration. In yet another embodiment, the anti-connexin polynucleotide composition is applied at about 1-15 $\mu$M final concentration. Anti-connexin polynucleotide dose amounts include, for example, about 0.1-1, 1-2, 2-3, 3-4, or 4-5 micrograms $\mu$g, from about 5 to about 10 $\mu$g, from about 10 to about 15 $\mu$g, from about 15 to about 20 $\mu$g, from about 20 to about 30 $\mu$g, from about 30 to about 40 $\mu$g, from about 40 to about 50 $\mu$g, from about 50 to about 75 $\mu$g, from about 75 to about 100 $\mu$g, from about 100 $\mu$g to about 250 $\mu$g, and from 250 $\mu$g to about 500 $\mu$g. Dose amounts from 0.5 to about 1.0 milligrams or more or also provided, as noted above. Dose volumes will depend on the size of the site to be treated, and may range, for example, from about 25-100 $\mu$L to about 100-200 $\mu$L, from about 200-500 $\mu$L to about 500-1000 $\mu$L (microliter) doses are also appropriate for larger treatment sites. As noted herein, repeat applications are contemplated. Repeat applications are typically applied about once per week, or when wound-healing may appear to be stalled or slowing.

Conveniently, the anti-connexin polynucleotide is administered in a sufficient amount to downregulate expression of a connexin protein, or modulate gap junction formation for at least about 0.5 to 1 hour, at least about 1-2 hours, at least about 2-4 hours, at least about 4-6 hours, at least about 6-8 hours, at least about 8-10 hours, at least about 12 hours, or at least about 24 hours post-administration.

The dosage of each of the anti-connexin polynucleotides in the compositions and methods of the subject invention may also be determined by reference to the concentration of the composition relative to the size, length, depth, area or volume of the area to which it will be applied. For example, in certain topical and other applications, e.g., instillation, dosing of the pharmaceutical compositions may be calculated based on mass (e.g. micrograms) of or the concentration in a pharmaceutical composition (e.g. $\mu$g/$\mu$l) per length, depth, area, or volume of the area of application.

The initial and any subsequent dosages administered will depend upon factors noted herein. Depending on the oligonucelotide, the dosage and protocol for administration will vary, and the dosage will also depend on the method of administration selected, for example, local or topical administration.

The doses may be administered in single or divided applications. The doses may be administered once, or application may be repeated.

One or more anti-connexin polynucleotides may be administered by the same or different routes. The various agents of the invention can be administered separately at different times during the course of therapy, or concurrently in divided or single combination forms.

Preferably one or more anti-connexin polynucleotides useful for wound healing are delivered by topical administration (peripherally or directly to a site), including but not limited to topical administration using solid supports (such as dressings and other matrices) and medicinal formulations (such as gels, mixtures, suspensions and ointments). In one embodiment, the solid support comprises a biocompatible membrane or insertion into a treatment site. In another embodiment, the solid support comprises a dressing or matrix. In one embodiment of the invention, the solid support composition may be a slow release solid support composition, in which the one or more anti-connexin polynucleotides useful for wound healing is dispersed in a slow release solid matrix such as a matrix of alginate, collagen, or a synthetic bioabsorbable polymer. Preferably, the solid support composition is sterile or low bio-burden. In one embodiment, a wash solution comprising one or more anti-connexin polynucleotides can be used.

The delivery of one or more anti-connexin polynucleotides may occur over a period of time, in some instances for about 0.5 hours, 1-2 hours, about 2-4 hours, about 4-6 hours, about 6-8, or about 24 hours or longer, may be a particular advantage in more severe wounds. In some instances, cell loss may extend well beyond the site of a procedure to surrounding cells. Such loss may occur within 24 hours of the original procedure and is mediated by gap junction cell-cell communication. Administration of anti-connexin polynucleotide(s) will modulate communication between the cells and minimize additional cell loss or injury or consequences of injury.

While the delivery period will be dependent upon both the site at which the downregulation is to be induced and the therapeutic effect which is desired, continuous or slow-release delivery for about 0.5 hours, about 1-2 hours, about 2-4 hours, about 4-6 hours, about 6-8, or about 24 hours or longer is provided. In accordance with the present invention, this maybe achieved by inclusion of the anti-connexin polynucleotides in a formulation together with a pharmaceutically acceptable carrier or vehicle, particularly in the form of a formulation for continuous or slow-release administration.

As noted, the one or more agents of the invention may be administered before, during, immediately following wounding, for example, or within about 180 or more, about 120, about 90, about 60, or about 30 days, of wounding, for example.

The routes of administration and dosages described herein are intended only as a guide since a skilled physician will determine the optimum route of administration and dosage for any particular patient and wound.

Any of the methods of treating a subject having or suspected of having or a disease, disorder, and/or wound, referenced or described herein may utilize the administration of any of the doses, dosage forms, formulations, and/or compositions herein described.

Dressings and Matrices

In one aspect, the one or more anti-connexin polynucleotides are provided in the form of a dressing or matrix. In certain embodiments, the one or more agents of the invention are provided in the form of a liquid, semi solid or solid composition for application directly, or the composition is applied to the surface of, or incorporated into, a solid contacting layer such as a dressing gauze or matrix. The dressing composition may be provided for example, in the form of a fluid or a gel. The one or more anti-connexin polynucleotides may be provided in combination with conventional pharmaceutical excipients for topical application. Suitable carriers include: Pluronic gels, Polaxamer gels, Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also include creams/ointments used for topical pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolality such as sodium chloride, and stabilizers such as EDTA.

In one embodiment one or more anti-connexin polynucleotides, for example a connexin 43 antisense polynucleotide, preferably a connexin 43 antisense oligodeoxynucleotide, is administered on a natural or synthetic matrix.

Suitable dressings or matrices may include, for example, the following with one or more anti-connexin polynucleotides. An anti-connexin 43 oligonucleotide is preferred, for example an anti-connexin 43 antisense oligonucleotide:

1) Absorptives: suitable absorptives may include, for example, absorptive dressings, which can provide, for example, a semi-adherent quality or a non-adherent layer, combined with highly absorptive layers of fibers, such as for example, cellulose, cotton or rayon. Alternatively, absorptives may be used as a primary or secondary dressing.

2) Alginates: suitable alginates include, for example, dressings that are non-woven, non-adhesive pads and ribbons composed of natural polysaccharide fibers or xerogel derived from seaweed. Suitable alginates dressings may, for example, form a moist gel through a process of ion exchange upon contact with exudate. In certain embodiments, alginate dressings are designed to be soft and conformable, easy to pack, tuck or apply over irregular-shaped areas. In certain embodiments, alginate dressings may be used with a second dressing.

3) Antimicrobial Dressings: suitable antimicrobial dressings may include, for example, dressings that can facilitate delivery of bioactive agents, such as, for example, silver and polyhexamethylene biguanide (PHMB), to maintain efficacy against infection, where this is needed or desirable. In certain embodiments, suitable antimicrobial dressings may be available as for example, as sponges, impregnated woven gauzes, film dressings, absorptive products, island dressings, nylon fabric, non-adherent barriers, or a combination of materials.

4) Biological & Biosynthetics: suitable biological dressings or biosynthetic dressings may include, for example, gels, solutions or semi-permeable sheets derived from a natural source. In certain embodiments, a gel or solution is applied to the treatment site and covered with a dressing for barrier protection. In another embodiment, a sheet is placed in situ which may act as membrane, remaining in place after a single application.

5) Collagens: suitable collagen dressings may include, for example, gels, pads, particles, pastes, powders, sheets or solutions derived from for example, bovine, porcine or avian sources or other natural sources or donors. In certain embodiments, the collagen dressing may interact with treatment site exudate to form a gel. In certain embodiments, collagen dressing may be used in combination with a secondary dressing.

6) Composites: suitable composite dressings may include, for example, dressings that combine physically distinct components into a single product to provide multiple functions, such as, for example, a bacterial barrier, absorption and adhesion. In certain embodiment, the composite dressings are comprised of, for example, multiple layers and incorporate a semi- or non-adherent pad. In certain embodiment, the composite may also include for example, an adhesive border of non-woven fabric tape or transparent film.

7) Contact Layers: suitable contact layer dressings may include, for example, thin, non-adherent sheets placed on an area to protect tissue from for example, direct contact with other agents or dressings applied to the treatment site. In certain embodiments, contact layers may be deployed to conform to the shape of the area of the treatment site and are porous to allow exudate to pass through for absorption by an overlying, secondary dressing.

8) Elastic Bandages: suitable elastic bandages may include, for example, dressings that stretch and conform to the body contours. In certain embodiment, the fabric composition may include for example, cotton, polyester, rayon or nylon. In certain other embodiments, the elastic bandage may for example, provide absorption as a second layer or dressing, to hold a cover in place, to apply pressure or to cushion a treatment site.

9) Foams: suitable foam dressings may include, for example, sheets and other shapes of foamed polymer solutions (including polyurethane) with small, open cells capable of holding fluids. Exemplary foams may be for example, impregnated or layered in combination with other materials. In certain embodiment, the absorption capability may be adjusted based on the thickness and composition of the foam. In certain other embodiments, the area in contact with the treatment site may be non-adhesive for easy removal. In yet another embodiment, the foam may be used in combination with an adhesive border and/or a transparent film coating that can serve as an anti-infective barrier.

10) Gauzes & Non-Woven dressings: suitable gauze dressings and woven dressings may include, for example, dry woven or non-woven sponges and wraps with varying degrees of absorbency. Exemplary fabric composition may include, for example, cotton, polyester or rayon. In certain embodiment, gauzes and non-woven dressing may be available sterile or non-sterile in bulk and with or without an adhesive border. Exemplary gauze dressings and woven dressings may be used for cleansing, packing and covering a variety of wound treatment sites.

11) Hydrocolloids: suitable hydrocolloid dressings may include, for example, wafers, powders or pastes composed of gelatin, pectin or carboxymethylcellulose. In certain embodiment, wafers are self-adhering and available with or without an adhesive border and in a wide variety of shapes and sizes. Exemplary hydrocolloids are useful on areas that require contouring. In certain embodiments, powders and pastes hydrocolloids may use used in combination with a secondary dressing.

12) Hydrogels (Amorphous): suitable amorphous hydrogel dressings may include, for example, formulations of water, polymers and other ingredients with no shape, designed to donate moisture and to maintain a moist healing environments and or to rehydrate the treatment site. In certain embodiment, hydrogels may be used in combination with a secondary dressing cover.

13) Hydrogels: Impregnated Dressings: suitable impregnated hydrogel dressings may include, for example, gauzes and non-woven sponges, ropes and strips saturated with an amorphous hydrogel. Amorphous hydrogels may include for example, formulations of water, polymers and other ingredients with no shape, designed to donate moisture to a dry treatment site and to maintain a moist healing environment.

14) Hydrogel Sheets: suitable hydrogel sheets may include for example, three-dimensional networks of cross-linked hydrophilic polymers that are insoluble in water and interact with aqueous solutions by swelling. Exemplary hydrogels are highly conformable and permeable and can absorb varying amounts of drainage, depending on their composition. In certain embodiment, the hydrogel is non-adhesive against the treatment site or treated for easy removal.

15) Impregnated Dressings: suitable impregnated dressings may include, for example, gauzes and non-woven sponges, ropes and strips saturated with a solution, an emulsion, oil, gel or some other pharmaceutically active compound or carrier agent, including for example, saline, oil, zinc salts, petrolatum, xeroform and scarlet red as well as the compounds described herein.

16) Silicone Gel Sheets: suitable silicone gel sheet dressings may include, for example, soft covers composed of cross-linked polymers reinforced with or bonded to mesh or fabric.

17) Solutions: suitable liquid dressings may include, for example, mixtures of multiprotein material and other elements found in the extracellular matrix. In certain embodiment, exemplary solutions may be applied to the treatment site after debridement and cleansing and then covered with an absorbent dressing or a nonadherent pad.

18) Transparent Films: suitable transparent film dressings may include polymer membranes of varying thickness coated on one side with an adhesive. In certain embodiments, transparent films are impermeable to liquid, water and bacteria but permeable to moisture vapor and atmospheric gases. In certain embodiments, the transparency allows visualization of the treatment site.

19) Fillers: suitable filler dressings may include, for example, beads, creams, foams, gels, ointments, pads, pastes, pillows, powders, strands or other formulations. In certain embodiment, fillers are non-adherent and may include a time-released antimicrobial. Exemplary fillers may be useful to maintain a moist environment, manage exudate, and for treatment of for example, partial- and full-thickness wounds, infected wounds, draining wounds and deep wounds that require packing.

Thus, in accordance with the invention, there are provided formulations by which cell-cell communication can be downregulated in a transient and site-specific manner for treatment of wounds that do not heal at expected rates. The formulations therefore have application in methods of therapy.

Wound Treatment

In instances of tissue damage (particularly with wounds characterized by delayed healing and chronic wounds) the formulations of the invention have been found effective in both promoting the wound healing process, reducing inflammation and in minimizing scar tissue formation. The formulations therefore have clear benefit in the treatment of wounds that do not heal at expected rates, whether the result of external trauma, or disease state (such as diabetic ulcers) or condition (such as venous ulcers, arterial ulcers, and vasculitic ulcers) or physical processes (such as pressure ulcers).

In one aspect the invention is directed to a method of promoting or improving wound healing in a subject suffering from or a chronic wound, delayed healing wound or incomplete healing wound, or other wounds that do not heal at expected rates, comprising administration of a therapeutically effective amount of one or more anti-connexin polynucleotides. In certain embodiments, the administration of one or more anti-connexin polynucleotides is effective to reduce granulation tissue deposition, promote cell migration to accelerate wound closure and healing, to facilitate epithelial growth, or any combination thereof.

In one aspect the invention is directed to a method of promoting or improving wound healing in a subject, comprising administration of one or more anti-connexin polynucleotides in an amount effective to regulate epithelial basal cell division and growth in a chronic wound, delayed healing wound or incomplete healing wound, or other wound that does not heal at an expected rate. In one embodiment, the anti-connexin polynucleotide is a connexin antisense polynucleotide effective to regulate epithelial basal cell division and growth. In one embodiment, the connexin antisense polynucleotide is a connexin 26 antisense polynucleotide, a connexin 43 antisense polynucleotide, or a mixture thereof.

In one aspect the invention is directed to a method of promoting or improving wound healing, comprising administration of one or more anti-connexin polynucleotides in an amount effective to regulate outer layer keratin secretion in a chronic wound, delayed healing wound or incomplete healing wound, or other wound that does not heal at an expected rate. In one embodiment, the anti-connexin polynucleotide is a connexin antisense polynucleotide effective to regulate outer layer keratin secretion. In one embodiment, the connexin antisense polynucleotide is a connexin 43 antisense polynucleotide, a 31.1 antisense polynucleotide, or a mixture thereof.

In one aspect the invention is directed to a method of reducing, preventing or ameliorating tissue damage in a subject suffering from a chronic wound, delayed healing wound or incomplete healing wound, or other wound that does not heal at an expected rate, comprising administration of one or more anti-connexin polynucleotides.

In one aspect the invention is directed to sustained administration of one or more anti-connexin polynucleotides. In one embodiment, the anti-connexin polynucleotides are administered for at least about 1-24 hours, at least about 0.5 hours, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours or at least about 24 hours. In one embodiment, connexin expression is downregulated over a sustained period of time. Preferably connexin 43 expression is downregulated for a sustained period of time. Conveniently, connexin 43 expression is downregulated for at least about 0.5, 1, 2, 4, 6, 8, 10, 12, or 24 hours. Full connexin recovery is generally within at least about 48-72 hours following downregulation of expression. Suitable subjects include a diabetic subject or other subject having a wound that does not heal at an expected rate.

In one aspect, the present invention provides a method of treating a subject having a chronic wound, delayed healing wound or incomplete healing wound, or other wound that does not heal at an expected rate, which comprises sustained administration of an effective amount of one or more anti-connexin polynucleotides. In a further aspect, the present invention provides a method of promoting or improving wound healing in a subject which comprises sustained administration of one or more anti-connexin polynucleotides to a chronic wound, delayed healing wound or incomplete healing wound, or other wound that does not heal at an expected rate.

According to another further aspect, the present invention provides a method of promoting or improving wound healing in a subject having a chronic wound, delayed healing wound or incomplete healing wound, or other wound that does not heal at an expected rate, which comprises sustained administration of one or more anti-connexin polynucleotides to a wound area in an amount effective to increase re-epithlialization rates in the wound area. In one embodiment the method comprises sustained administration of a connexin 43 antisense polynucleotide, and/or a connexin 31.1 antisense polynucleotide. In one embodiment, the composition or compositions are administered in a sustained release formulation. In another embodiment, the composition or compositions are administered for a sustained period of time. Conveniently, the composition is effective to decrease connexin 43 and/or 31.1 levels or expression for at least about 24 hours. Subjects which may be treated include diabetic subjects, or other subjects having a wound that does not heal at an expected rate.

In yet another aspect, the present invention provides invention provides a method of promoting or improving wound healing in a subject having a chronic wound, delayed healing wound or incomplete healing wound, or other wound that does not heal at an expected rate, which comprises sustained administration one or more anti-connexin polynucleotides to a wound area in an amount effective to effective to regulate epithelial basal cell division and growth and/or effective to regulate outer layer keratin secretion. In one embodiment, the composition comprises a connexin antisense polynucleotide effective to regulate epithelial basal cell division or growth, preferably a connexin 26 antisense polynucleotide, a connexin 43 antisense polynucleotide, or a mixture thereof. In one embodiment, the composition comprises a connexin antisense polynucleotide effective to regulate outer layer keratinization, preferably, a connexin 31.1 antisense polynucleotide. In one embodiment, the composition or compositions are administered in a sustained release formulation. In another embodiment, the composition or compositions are administered for a sustained period of time. Conveniently, the composition is effective to decrease connexin 43, 26, and/or 31.1 levels or expression for at least about 24 hours. Subjects which may be treated include diabetic subjects.

In one aspect the invention is directed to a method for treatment or prophylaxis of a chronic wound, delayed healing wound or incomplete healing wound, or other wound that does not heal at an expected rate, comprising administering to a subject in need thereof an effective amount of an anti-connexin polynucleotide administered to said wound or a tissue associated with said wound. In another embodiment, the chronic wound is a chronic skin wound and a composition of the present invention is administered to the skin or a tissue associated with the skin of said subject for an effective period of time. Conveniently, the composition is effective to decrease connexin 43 levels, or block or reduce connexin 43 hemichannel opening, for at least about 0.5 hours, about 1-2 hours, about 2-4 hours, about 4-6 hours, about 4-8 hours, about 12 hours, about 18 hours, or about 24 hours. A chronic skin wound suitable for treatment may, for example, be selected from the group consisting of pressure ulcers, diabetic ulcers, venous ulcers, arterial ulcers, vasculitic ulcers, and mixed ulcers. The chronic wound may be an arterial ulcer, which comprises ulcerations resulting from complete or partial arterial blockage. The chronic wound may be a venous stasis ulcer, which comprises ulcerations resulting from a malfunction of the venous valve and the associated vascular disease. The chronic wound may be a trauma-induced ulcer. Subjects with other ulcers, including venous ulcers and others described herein and known in the art.

Compositions

The present invention is directed to pharmaceutical compositions, formulations, and their methods of manufacture and use wherein the composition comprises therapeutically effective amounts of an anti-connexin polynucleotide, including, for example, a connexin antisense polynucleotide. The compositions are useful in enhancing or promoting healing of wounds that do not heal at expected rates, including wounds that may be slow to heal or refractory to conventional wound treatment or wound healing promoting therapies.

In one preferred form, the composition contains one or more anti-connexin polynucleoptides, for example a connexin antisense polynucleotide, to the mRNA of one connexin protein only. Most preferably, this connexin protein is connexin 43.

Alternatively, the compositions may comprise polynucleotides to more than one connexin protein. Preferably, one of the connexin proteins to which polynucleotides are directed is connexin 43. Other connexin proteins to which oligodeoxynucleotides are directed may include, for example, connexins 26, 30, 31.1, 32, and 37. Suitable exemplary polynucleotides (and ODNs) directed to various connexins are set forth in Table 1.

Many aspects of the invention are described with reference to oligodeoxynucleotides. However it is understood that other suitable polynucleotides (such as RNA polynucleotides) may be used in these aspects. Other anti-connexin oligonucleotides are RNAi and siRNA oligonucleotides.

Accordingly, in one aspect, the invention provides compositions for use in therapeutic treatment, which comprises at least one anti-connexin polynucleotide, preferably an anti-connexin 43 polynucleotide. In a preferred embodiment, the composition further comprises a pharmaceutically acceptable carrier or vehicle.

Kits, Medicaments and Articles of Manufacturer

Optionally, one or more anti-connexin polynucleotides may also be used in the manufacture of the medicament. In one embodiment, the medicament comprises a therapeutically effective amount of an anti-connexin polynucleotide, preferably an anti-connexin 43 polynucleotide, and a pharmaceutically acceptable carrier.

In one aspect, the invention provides a kit comprising one or more compositions or formulations described. For example, the kit may include a composition comprising an effective amount of one or more connexin 43 antisense polynucleotides.

Articles of manufacturer are also provided, comprising a vessel containing a composition or formulation of the invention as described herein and instructions for use for the treatment of a subject. For example, an article of manufacturer, comprising a vessel containing a connexin antisense polynucleotide and instructions for use for the treatment of a subject suffering from a chronic, delayed healing, or incomplete healing wound, or other wound that does not heal at an expected rate.

In another aspect, the invention includes an article of manufacture comprising a vessel containing a therapeutically effective amount of one or more anti-connexin polynucleotides and instructions for use, including use for the treatment of a subject having a chronic wound or a delayed or incomplete healing wound, or other wound that does not heal at an expected rate. In another aspect, the invention includes an article of manufacture comprising a vessel containing a therapeutically effective amount of one or more anti-connexin polynucleotides and instructions for use, including use for the treatment of a subject having or suspected of having any diseases, disorders and/or conditions characterized in whole or in part by a chronic wound or delayed or incomplete wound healing, or other wound that does not heal at an expected rate.

As noted, wound healing has been reported to be slow in diabetes, often resulting in infection or chronic wounds that can lead to amputation. Cell-cell communication through the gap junction protein connexin 43 and the dynamic regulation of connexin 43 expression are reported to play pivotal roles in wound healing. In normal tissue, such as skin, in the first 24 hours after wounding, connexin 43 is normally down-regulated and connexin 26 upregulated in keratinocytes at the edge of the wound as they adopt a migratory phenotype. However, in diabetic tissue, in general, and skin, in particular, we have found that connexin 43 to be upregulated immediately after wounding.

Wound healing in the diabetic rat has been used as one model of chronic wounding. Example 1 demonstrates the use of anti-connexin oligonucleotide to improve impaired wound-healing in the diabetic rat. In Example 1, acute, streptozotocin-induced diabetes in rats alters connexin expression in skin, decreasing connexin 43 and connexin 26 protein and communication in the epidermis and increasing connexin 43 protein and communication in the dermis. Example 1 demonstrates that diabetes alters the dynamic changes of connexins associated with wound healing. Within 24 hours, connexin 43 was upregulated in a thickened bulb of keratinocytes at the wound edge (rather than downregulated, as in controls which formed a thin process of migratory cells). Connexin 43 decline was delayed until 48 hours when re-epithelialization then began. Although connexin 26 was upregulated as usual in diabetes, its distribution at the wound edge was abnormal, being more widespread. Example 1 further shows the association between the abnormal dynamics of connexin 43 expression and delayed re-epithelialization as confirmed by application of a connexin 43-specific antisense gel to diabetic wounds compared by application of a gel with the corresponding sense oligodeoxynucleotide. This treatment prevented abnormal upregulation of connexin 43 and doubled the rate of re-epithelialization to control (nonrdiabetic) levels and above.

The results reported in Example 1 support the conception that diabetes-induced changes in connexin expression dynamics contribute to delayed wound healing and that targeting connexin 43 expression as a means to promote healing of diabetic and other chronic wounds is of potential therapeutic value.

Example 2 demonstrates the successful application of an anti-connexin 43 oligonucleotide to promote healing of a non-healing skin ulcer in a human subject.

Example 3 demonstrates the successful application of an anti-connexin 43 oligonucleotide to promote healing of a non-healing venous ulcer in a human subject.

Various aspects of the invention will now be described with reference to the following examples, which will be understood to be provided by way of illustration only and not to constitute a limitation on the scope of the invention.

EXAMPLES

Example 1

Oligodeoxynucleotides were prepared with the following sequences:

```
                                        (SEQ. ID. NO: 2)
GTA ATT GCG GCA GGA GGA ATT GTT TCT CTC
(connexin 43)

(SEQ. ID. NO: 7)
GAC AGA AAC AAT TCC TCC TGC CGC ATT TAC
(sense control)
```

Diabetes was induced in adult Sprague-Dawley rats (350-400 g) by a single intraperitoneal injection containing streptozotocin, 65 mg/kg, in citrate buffer (Shotton H R, et al. (2003) *Diabetes*. 52:157-64) (N=six diabetic, six control). Most diabetic wound-healing studies have been carried out two weeks after diabetes induction and the same time point was used for this wound healing study. However, connexin expression in diabetic rat skin was also examined at eight weeks (N=six diabetic, six control) to confirm that the changes detected at two weeks remained the same. Normal back skin was excised, cryosectioned, immunostained for connexins, imaged by confocal microscopy and the staining quantified as in Saitongdee et al. (2000). *Cardiovascular Res.* 47, 108-115.

Rats were anaesthetised with halothane and their backs were shaved. Two pairs of 5×5 mm full thickness excisional wounds were made, and 1004 connexin 43-specific antisense oligodeoxynucleotide in Pluronic F-127 gel was applied to one wound and control (sense) gel to the other (Qiu C, et al. (2003) *Cell Biol. Int.* 27:525-541). Tissue was harvested on days 1, 2, 5, 10 and 15 after wounding, and sectioned in preparation for connexin immunohistochemistry or H&E staining (Id.) Dynamic changes in connexin expression correlate with key events in the wound healing process. N=six diabetic, six control rats per time point.

Intercellular communication was assessed by applying a 4% solution of Lucifer Yellow CH (Sigma) in a pledget of gelfoam into a fresh, full thickness skin incision. Dye was allowed to transfer for 5 minutes prior to removal of the gel foam and fixation of the tissue. A 10 kD Kd FITC-dextran that will enter injured cells but not pass through gap junctions was used as a control. Tissues were cryosectioned and imaged by confocal microscopy on a Leica SP2UV (Leica, Milton Keynes, UK; N=four diabetes and four control).

Transferred dyes and connexin immunostaining were examined using the confocal microscope. Optimal gain and offset were set in advance and kept constant during image acquisition. A series of single optical section images was taken to generate a montage of the skin from the cut. Digital images were eight bit and were analysed using Image-J software (NIH). To assess dye transfer, a 1500×30 pixel region-of-interest box was placed from the cut edge in the mid-dermis and an image intensity graph across the box was generated. A grey level intensity drop below 50 was arbitrarily taken as the point where Lucifer Yellow had travelled. Similarly, in the epidermis, the distance from the cut to where the Lucifer Yellow signal dropped below 50 was recorded. A minimum of three images were analysed from each animal. To compare levels of connexin protein, six single optical section images of dermis or epidermis were taken from different sections for each wound. All parameters of laser power, pinhole, gain/offset and objective were kept constant across both control and diabetic groups. Connexin expression was quantified, as in Saitongdee et al. (2000) supra, using ImageJ software (NIH). A threshold was set to detect gap junction plaques with minimal background noise and was then kept constant for all images. The number and size of connexin plaques were recorded for each image and expressed per 100 µm of epidermis or 10000 µm$^2$ of dermis. This approach has proved to be much more accurate than Western blot as it generates information on protein expression at the cellular level. Western blots would be unable to distinguish between epidermal and dermal cells or detect effects of proximity to the wound edge. Using this approach, connexin levels in keratinocytes in a zone at the wound edge (WE) and in a zone 500 µm away (AD), were able to be quantified either one or two days after wounding. At day five after wounding an additional zone of the leading edge (LE) of the nascent epidermis was also imaged. Images of H&E staining were taken using a Leica DMLFS microscope with a DC300F digital camera. Measurements for re-epithelialization rate have been described in detail previously (Qiu C, et al. (2003) supra. All numerical differences between treatments were tested for significance using the Wilcoxon matched-pairs signed-ranks test as implemented in Statview 5.0.1.

FIGS. 1A and 1B depict connexin 43 and 26 staining in normal and STZ diabetic rat skin at two weeks (FIG. 1A) and eight weeks after induction of diabetes (FIG. 1B). Graphs show the numbers of plaques in the epidermis and dermis. Connexin 43 and connexin 26 staining is significantly reduced in the diabetic epidermis whilst connexin 43 staining is increased in the dermis as early as two weeks after induction of diabetes, with no further change at eight weeks. FIG. 1C depicts images of typical connexin 43 and connexin 26 immunostaining in control, C, and diabetic, D skin, at eight weeks, where arrowheads mark the boundary between the epidermis and dermis. Scale bar 25 µm. FIG. 1D quantification of the distance that the gap-junction-permeant dye, Lucifer Yellow, traveled in five minutes in the epidermis and dermis of control and diabetic rats. Dye transfer was significantly reduced in the diabetic epidermis but significantly increased in the diabetic dermis.

Typically punctate connexin 43 immunostaining was found in the basal layer of the epidermis, and in dermal fibroblasts, hair follicles, blood vessels and appendages (FIGS. 1A to 1D). However, in diabetic skin, connexin 43 staining was significantly reduced in the epidermis, in terms of both size and number of gap junction plaques (FIG. 1A). Staining for connexin 26 in the upper layers of the epidermis was similarly significantly reduced in diabetic epidermis (FIG. 1A). However, this was not a global downregulation of connexins in response to diabetes as a contrasting effect was observed in dermal fibroblasts; in these, a distinct increase in the size and number of connexin 43-positive plaques was observed. Similar effects on connexin expression were seen in skin two weeks and eight weeks after STZ induction of diabetes (FIG. 1B).

To assess cell-cell communication in diabetic epidermis and dermis, the extent of transfer of the gap-junctionpermeant dye Lucifer Yellow through the tissue in five minutes was examined. This revealed significantly reduced communication in the diabetic epidermis but significantly enhanced communication in the dermis (FIG. 1D), consistent with the changes in connexin protein expression. Elevated expression of connexin 43 protein and increased communication has been reported in human diabetic fibroblasts (Abdullah K M, et al. (1999) *Endocrine* 10:35-41.) and mixed responses of different connexins to diabetes have been noted in the renal system (Zhang J, Hill C E. (2005) *Kidney Int.* 68:1171-1185.) and bladder (Poladia D P, et al. (2005) *Acta Diabetol.* 42:147-152.)).

FIGS. 2A to 2D depict re-epithelialization rates and responses of connexin 43 and connexin 26 protein levels following injury in control and diabetic epidermis. Staining was quantified, by counting plaques, at one and two days after wounding in epidermis at the wound edge (WE) and adjacent (AD) epidermis, 500 µm away (FIG. 2A. On day five, an additional zone at the leading edge (LE) of the nascent epidermis was quantified and the data was also included. The rate of re-epithelialization was significantly reduced in diabetic rats (D) as compared with controls (C) at all time points: one, two and five days post wounding (FIG. 2B). Connexin 43 staining in zone WE normally reduces in the first 24 hours after injury but in diabetic skin it increases significantly, returning to near control levels by 2 dpw, and is found at significantly reduced levels in all three zones 5 dpw (FIG. 2C). The normal response of connexin 26 to injury is to increase the level of staining in WE and this occurred in both control and diabetic animals at 1 dpw (FIG. 2D). At 2 dpw, however, in diabetic skin, connexin 26 staining was seen to be significantly elevated in both WE and AD zones, reducing significantly in these zones only at 5 dpw.

Figure 3C:
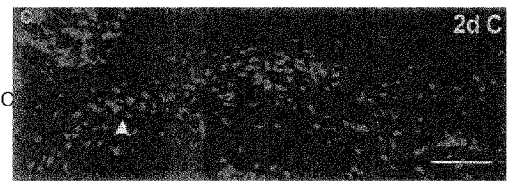
Figure 3D:
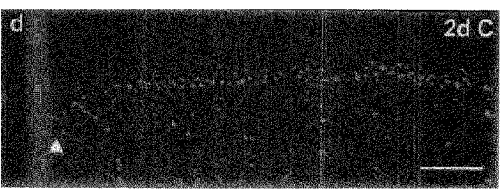
Figure 3C:
Figure 3D:
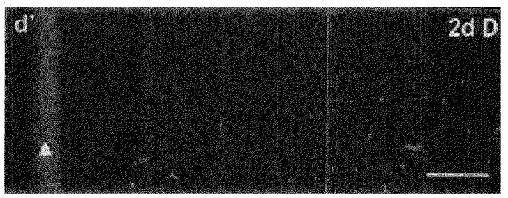
Figure 3E:
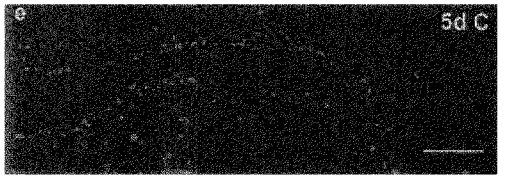
Figure 3F:
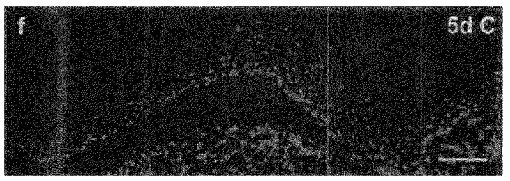
Figure 3E:
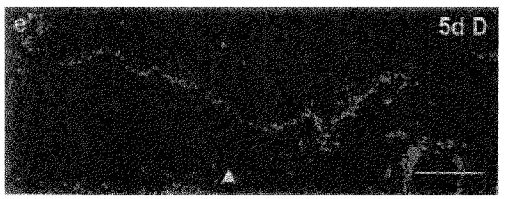
Figure 3F:
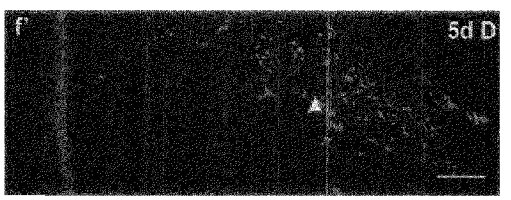

FIGS. 3a to 3f and 3a' to 3f depict connexin 43 (a, a', c, c', e, e') and connexin 26 (b, b', d, d', f, f) staining (green) and nuclear staining (blue) at the epidermal wound edge of control and diabetic skin during the wound-healing process. At one day, connexin 43 protein expression is down regulated in the leading-edge keratinocytes of control rats (FIG. 3a) but has been upregulated in this region, which appears swollen, in diabetic animals (FIG. 3a'). connexin 26 can be seen to upregulate similarly in both control (FIG. 3b) and diabetic (FIG. 3b') epidermis. At two days, connexin 43 staining has reduced in the diabetic leading-edge keratinocytes (FIG. 3c') and is similar that of controls (FIG. 3c) whilst connexin 26 has continued to increase in all diabetic keratinocytes (FIG. 3d') to significantly higher levels than controls (FIG. 3d). At five days after wounding the nascent epidermis of control (FIG. 3e) and diabetic (FIG. 3e') shows very little punctate connexin 43 staining between keratinocytes whilst connexin 26 staining is a little reduced in diabetic wounds (FIG. 3f) compared to control wounds (FIG. 3f). Arrowhead marks the edge of the wound. Scale bar a, c, e, 50 μm b, d, f 100 μm.

To determine the dynamic responses of connexin expression to injury, connexin staining in keratinocytes at the wound edge (WE) and in an adjacent zone 500 μm away (AD) was quantified, one and two days after wounding, whilst after five days the leading edge (LE) keratinocytes (FIG. 2A) was imaged. One day after wounding a significant reduction in connexin 43 staining in control keratinocytes was found in the WE zone compared to AD (FIGS. 2C, 3a and 3a'). In marked contrast, in diabetic animals a significant increase in connexin 43 staining was found in WE compared to AD. This was the opposite of the normal wound-healing response and was surprising because connexin 43 levels were significantly reduced in intact diabetic skin. The dynamic response of connexin 26 was similar in diabetic and control skin, with a significant increase in staining in the WE zone (FIGS. 2D, 3b and 3b') although, in diabetic skin, the elevation of connexin 26 staining was not restricted to WE zone as in controls but extended for some distance into the AD zone, implying a greater spread in the response to injury. In addition the keratinocytes at the wound edge were found to form a thickened bulb in diabetic tissue whereas they thinned out prior to crawling forward to close the wound in controls.

Two-day control wounds were starting to re-epithelialize (12% closed) but diabetic wounds were retarded (5% closed), having only recently adopted a migratory morphology. Accompanying this diabetic keratinocyte shape change there was a significant reduction in connexin 43 staining within the WE zone, which by this stage resembled that of controls (FIGS. 2C, 3c and 3c'). However, in diabetic skin wounds, levels of connexin 26 staining continued to rise in both the WE and AD zones (FIGS. 2D, 3d and 3d'), indicating a much wider tissue response to the injury.

On day five, re-epithelialization was well underway in both diabetic and control groups, though the diabetic wounds were significantly retarded (20% closed compared with 33% in controls; P<0.008; Wilcoxon matched-pairs signed-ranks test; FIG. 2C). In both diabetic and control groups, LE keratinocytes could be clearly seen to contain little connexin 43 staining Connexin 43 staining rose significantly in the WE and AD zones, but less in diabetic skin which, like intact skin, expressed less connexin 43 than controls (FIGS. 2C, 3e and 3e'). At this stage, connexin 26 staining in LE was similarly raised in both diabetic and control skin (FIGS. 2D, 3f and 3f). The previously elevated connexin 26 staining in diabetic WE and AD zones returned to more normal levels. Re-epithelialization was complete in both control and diabetic animals by day ten, when high levels of connexin 43 can be seen in the proliferative, excessively thickened epidermis.

Figure 4A:
FIGS. 4A to 4C depict effects of application of a connexin 43 antisense oligodeoxynucleotide composition on connexin 43 expression and wound healing.
Figure 4B:
Figure 4C:
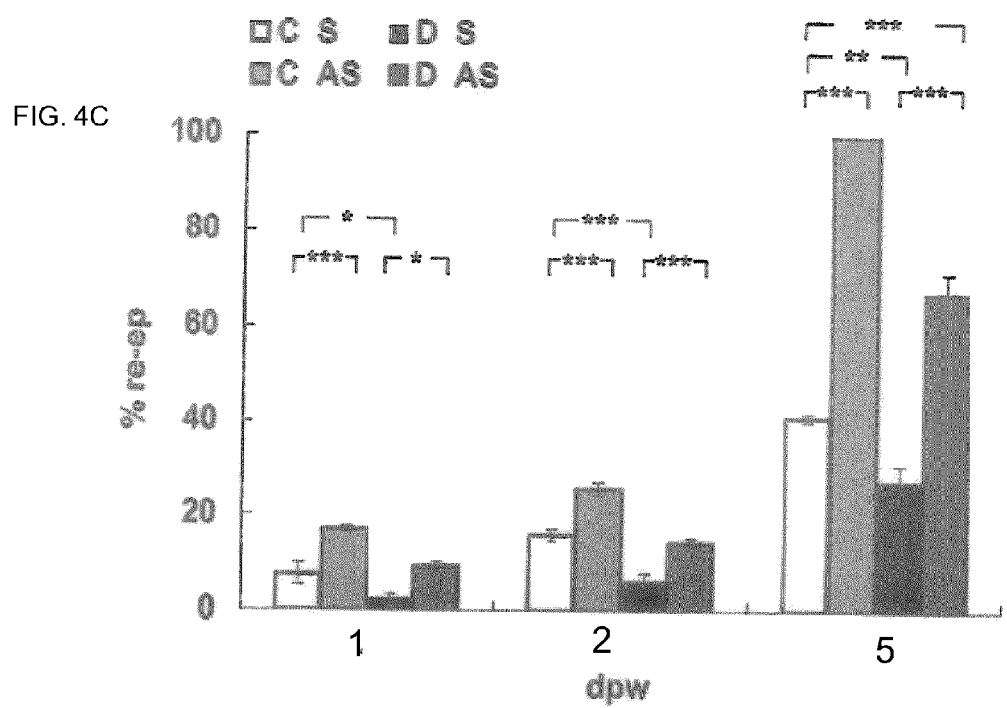

FIGS. 4A to 4C depict effect of connexin 43 antisense oligodeoxynucleotide ("Cx43asODN") treatment on connexin 43 expression one day post-wounding and on re-epithelialization rates at one, two and five days as compared with a connexin 43 sense oligodeoxynucleotide control ("sODN"). Elevated levels of connexin 43 staining (green puncta) can be seen in the swollen epidermal bulb at the edge of a diabetic wound 1 dpw (FIG. 4A). However, this elevation in connexin 43 protein expression was prevented by treatment with connexin 43asODNs which also results in a thinner layer of keratinocytes that appear more like control animals rather than a bulb of cells (FIG. 4B). Treating pairs of wounds in control and diabetic skin with asODNs or control sODNs results in double the rate of re-epithelialization following asODN application all time points examined (FIG. 4C). The rate of re-epithelialization of diabetic asODN treated skin approximates that of sODN treated control skin at 1 dpw and 2 dpw but is significantly faster at 5 dpw. Scale bar 50 μm.

Having observed these abnormal patterns of connexin immunostaining, gap junctional communication and morphological response in diabetic wounds, the effect of the abnormal increase of connexin 43 protein in diabetic WE keratinocytes was assessed by preventing the increase with a connexin 43-specific antisense gel, applied to the wound at the time of injury. This effectively prevented the increase in connexin 43 (FIG. 4A), and also improved wound-healing rates which doubled, reaching that of untreated control levels or more (FIG. 4B) although healing rates were even higher in antisense-treated wounds in control rats.

The mechanism whereby diabetes alters the expression of connexins, with a differential effect on different connexin proteins, is unknown. Hyperglycaemia and/or oxidative stress induced by hyperglycaemia have been implicated in the development of other complications of diabetes such as neuropathy and angiopathy (American Diabetes Association (1999) Consensus development conference on diabetic foot wound care: 7-8 Apr. 1999, Boston, Massachussets). Both high glucose and oxidative stress in vitro have been reported to alter connexin expression and/or gap junctional communication in a variety of different cell types (Fukuda T, et al. (2000) *J. Gastroenterol.* 35:361-368; Cho J H, et al. (2002), *Carcinogenesis.* July; 23(7):1163-9; Rouach N, et al. (2004) *Glia.* 1:45(1):28-38), and connexin 43 and connexin 26 are known to have different promoters (Hennemann H, et al. (1992) *Eur. J. Cell Biol.* 58(1):81-9); Chen Z Q, et al. (1995) *J Biol Chem.* 270(8):3863-8.

However, impaired wound healing has been demonstrated in rats as early as one week after induction of diabetes, before either neuropathy or angiopathy develops (Witte M B, et al. (2002) *Br. J. Surg.* 89:1594-1601); Shi H P, et al. (2003) *Wound Repair Regen.* 11:198-203). Thus, the changes observed in these experiments within two weeks are likely to be direct consequences of the diabetic condition rather than secondary consequences of long-term diabetic complications.

A significant finding was the abnormal upregulation of connexin 43 in the epidermal wound edge in diabetes. This has the potential to affect the process of wound closure in different ways. The formation of communication compartments within the regenerating epidermis has been proposed to play a role in wound healing (Martin P (1997) *Science* 276:75-81); Lampe P D, et al. (1998) *J Cell Biol.* 143(6): 1735-47; Hodgins M (2004) *J. Invest. Dermatol.* 122: commentary). Compartmentalization could be effectively brought about in normal conditions by expression of connexin 26 and removal of connexin 43 in leading edge cells, as these connexins do not form junctions with one another. Thus, the delay in wound healing in diabetes could reflect the additional time required for connexin 43 expression to downregulate to a point where such a compartmentalization can occur. Alternatively, the C-tail of connexin 43 is known to interact with cytoskeletal components or with P120ctn/ Rho GTPase, so downregulation of connexin 43 could be necessary for changing the motility of keratinocytes at the wound edge, enabling them to migrate and close the wound (Wei C J, et al. (2004) *Annu Rev Cell Dev Biol.* 20:811-38). In this regard, it was notable that, one day after wounding when their connexin 43 expression was high, diabetic keratinocytes formed a thickened bulb at the wound edge rather than flattening out and starting to crawl forward across the wound.

We have shown here that knocking down connexin 43 expression by a single application of the connexin 43-specific antisense gel at the time of wounding enables the entire process, from initial migration to complete wound closure, to occur at a normal and above rate despite the continued presence of the diabetic condition. Thus, anti-connexin oligonucleotide treatment, for example, antisense treatment, has considerable potential as a novel approach for the treatment of wounds that do not heal at expected rates, including chronic wounds in diabetic and other patients.

Example 2

The invention has been successfully used to treat a human subject with a large chronic wound, in this case a vasculitic ulcer, on a compassionate use basis.

A 49 year old male with underlying peripheral vascular disease first presented for complications arising from a non-closing leg wound. This patient had undergone a left below-knee amputation secondary to trauma, which subsequently dehisced as a result of a fall. Over a greater than 6-month period the wound had been unresponsive to all forms of established care. The patient underwent multiple topical treatments in an attempt to heal the wound, including the application of growth factor, antimicrobial dressings, VAC (vacuum assisted closure), xenograft dressing, with no significant change. The patient then fell and further injured the wound site. This was followed by multiple surgical debridements and replacement of the xenograft. The wound continued to increase in size and was considered to have become limb-threatening.

Thus, due to the nature of the wound and the level and type of amputation, the patient was considered to have had no alternative treatment option except to undergo an above-knee amputation. The Dermatology Division of the FDA approved use of applicants' experimental drug (SEQ ID NO: 1) for this patient under an Emergency Use IND. The wound was subsequently treated with 2 mL of 20 µM preparation of SEQ ID NO: 1 in pluronic gel (total dose 400 µg). The wound at the time of application was approximately 7 cm×5 cm (about 35 cm$^2$) with a depth of approximately 3-4 mm. Thus, about 12 µg/cm$^2$ of SED ID NO: 1 was administered. The wound was dressed and left covered for a period of 7 days. When uncovered on Day 7, the physician reported that both edema and erythema were no longer present and the wound appeared to have begun to granulate although the dimensions (length and width) were approximately the same at that stage.

A second treatment (total dose 400 µg) was applied. Following this treatment, the wound continued to heal and the lesion was subsequently reported to be 1 mm in depth (a three- to four-fold reduction) with 1-1.5 cm of new tissue on all sides. The wound was clean and granulation tissue "healthy" in appearance. The patient was considered "graft-ready" if other tissue, e.g., thigh tissue could be used for grafting. However, this was not considered an option for this patient because of his underlying peripheral vascular disease.

No safety concerns following this experimental treatment were evident or reported. The patient was assessed again at two months and the wound had continued to reduce in size. The approximate size of the wound had reduced by 7-fold, to 5 cm$^2$, and medical personnel assessing the wound concluded that it will proceed to full closure. It was determined that an above-knee-amputation was no longer required.

Example 3

The invention has been successfully used to treat a human subject with a venous chronic wound.

An 86 year old male with underlying peripheral edema presented with complications from a five-month old, non-healing chronic venous ulcer. Over this period the wound had been unresponsive to all forms of established care in the community. The patient underwent multiple topical treatments in an attempt to heal the wound, including antimicrobials and the application of a pressure bandage to reduce edema. Over this period of time the wound continued to increase in size. The patient was scheduled to undergo knee replacement surgery, but was informed that the operation could not proceed in the presence of an open chronic wound.

Thus, due to the nature of the wound, which was also inflamed and swollen within the wound bed and particularly at the edges, the patient was considered as a compassionate use case and informed consent was obtained in order to treat the patient. The wound was subsequently treated with 200 µL of 10 µM preparation of SEQ ID NO: 1 in pluronic gel (total dose of approximately 20 µg). The wound at the time of application was approximately 3 cm×3 cm (about 9 cm$^2$) with a depth of approximately 2-3 mm. Thus, the total dose applied was about 2.2 µg per cm$^2$. The wound was then dressed with a non-adhesive dressing for 24 hours.

When uncovered at 24 hours, inflammation and swelling were no longer present and the wound was drying. The wound was then left uncovered until 72 hours post-treatment at which time the previously non-healing skin ulcer wound was fully dried and a scab had formed over the entire wound. The wound was subsequently dressed and reexamined at one week, at which time the wound dimensions (length and width) had reduced significantly, inflammation and swelling remained absent, and the wound was healing and progressing toward closure.

A second treatment (total dose of approximately 20 µg of SEQ.ID.NO: 1) was applied at one month following a further injury to the wound, which had led to a cessation toward closure. Following this treatment, a pressure bandage was applied to reduce edema and the wound rapidly began to heal again. The lesion diminished in depth, width and length and the new skin where the wound healed was healthy in appearance.

No safety concerns following this experimental treatment were evident or reported. The patient was assessed again at six weeks. The wound had reduced in size to approximately one-quarter the original size, and was progressing to closure.

TABLE 2

Table 2A

Human Connexin 43 from GenBank Accession No. M65188
(SEQ. ID. NO: 13)

```
   1 ggcttttagc gtgaggaaag taccaaacag cagcggagtt ttaaacttta aatagacagg
  61 tctgagtgcc tgaacttgcc ttttcatttt acttcatcct ccaaggagtt caatcacttg
 121 gcgtgacttc actactttta agcaaaagag tggtgcccag gcaacatggg tgactggagc
 181 gccttaggca aactccttga caaggttcaa gcctactcaa ctgctggagg gaaggtgtgg
 241 ctgtcagtac ttttcatttt ccgaatcctg ctgctgggga cagcggttga gtcagcctgg
 301 ggagatgagc agtctgcctt tcgttgtaac actcagcaac ctggttgtga aaatgtctgc
 361 tatgacaagt ctttcccaat ctctcatgtg cgcttctggg tcctgcagat catatttgtg
 421 tctgtaccca cactcttgta cctggctcat gtgttctatg tgatgcgaaa ggaagagaaa
 481 ctgaacaaga aagaggaaga actcaaggtt gcccaaactg atggtgtcaa tgtggacatg
 541 cacttgaagc agattgagat aaagaagttc aagtacggta ttgaagagca tggtaaggtg
 601 aaaatgcgag gggggttgct gcgaacctac atcatcagta tcctcttcaa gtctatcttt
 661 gaggtggcct tcttgctgat ccagtggtac atctatggat tcagcttgag tgctgtttac
 721 acttgcaaaa gagatcccctg cccacatcag gtggactgtt tcctctctcg ccccacggag
 781 aaaaccatct tcatcatctt catgctggtg gtgtccttgg tgtccctggc cttgaatatc
 841 attgaactct tctatgtttt cttcaagggc gttaaggatc gggttaaggg aaagagcgac
 901 ccttaccatg cgaccagtgg tgcgctgagc cctgccaaag actgtgggtc tcaaaaatat
 961 gcttatttca atggctgctc ctcaccaacc gctccctct cgcctatgtc tcctcctggg
1021 tacaagctgg ttactggcga cagaaacaat tcttcttgcc gcaattacaa caagcaagca
1081 agtgagcaaa actgggctaa ttacagtgca gaacaaaatc gaatgggca ggcgggaagc
1141 accatctcta actcccatgc acagccttt gatttccccg atgataacca gaattctaaa
1201 aaactagctg ctggacatga attacagcca ctagccattg tggaccagcg accttcaagc
1261 agagccagca gtcgtgccag cagcagacct cggcctgatg acctggagat ctag
```

Table 2B

Human Connexin 43
(SEQ. ID. NO: 14)

```
   1 atgggtgactggagcgcctt aggcaaactc cttgacaagg ttcaagccta ctcaactgct
  61 ggagggaaggtgtggctgtc agtacttttc attttccgaatcctgctgct ggggacagcg
 121 gttgagtcagcctggggaga tgagcagtct gcctttcgtt gtaacactca gcaacctggt
 181 tgtgaaaatg tctgctatga caagtctttcccaatctctc atgtgcgctt ctgggtcctg
 241 cagatcatat ttgtgtctgt acccacactcttgtacctgg ctcatgtgttctatgtgatg
 301 cgaaaggaag agaaactgaa caagaaagag gaagaactca aggttgccca aactgatggt
 361 gtcaatgtgg acatgcactt gaagcagatt gagataaagaagttcaagta cggtattgaa
 421 gagcatggta aggtgaaaat gcgaggggg ttgctgcgaa cctacatcat cagtatcctc
 481 ttcaagtcta tctttgaggt ggccttcttg ctgatccagt ggtacatcta tggattcagc
 541 ttgagtgctg tttacacttg caaaagagat ccctgcccac atcaggtgga ctgtttcctc
 601 tctcgcccca cggagaaaac catcttcatc atcttcatgc tggtggtgtc cttggtgtcc
 661 ctggccttga atatcattga actcttctat gttttcttca agggcgttaa ggatcgggtt
 721 aagggaaaga gcgacccttaccatgcgacc agtggtgcgc tgagccctgc caaagactgt
 781 gggtctcaaa aatatgctta tttcaatggc tgctcctcac caaccgctcc cctctcgcct
 841 atgtctcctc ctgggtacaa gctggttact ggcgacagaa acaattcttc ttgccgcaat
 901 tacaacaagc aagcaagtga gcaaaactgg gctaattaca gtgcagaaca aaatcgaatg
 961 gggcaggcgg gaagcaccat ctctaactcc catgcacagc cttttgattt ccccgatgat
1021 aaccagaatt ctaaaaactagctgctgga catgaattac agccactagc cattgtggac
1081 cagcgacctt caagcagagc cagcagtcgt gccagcagca gacctcggcctgatgacctg
1141 gagatctag
```

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method of treating a subject having a wound not healing at an expected rate, which comprises administration of an effective amount of an article of manufacture comprising an anticonnexin 43 polynucleotide present at a concentration from 1.0 to about 40.0 milligrams per milliliter to the wound.

2. A method according to claim 1 wherein the anticonnexin 43 polynucleotide is selected from the group consisting of a connexin 43 antisense polynucleotide, an RNAi polynucleotide, and an siRNA polynucleotide.

3. A method according to claim 1 wherein the anticonnexin 43 polynucleotide is administered for at least about 0.5 hours, at least about 1-2 hours, at least about 2-4 hours, at least about 4-6 hours, or at least about 6-8 hours.

4. A method according to claim 1 wherein the wound is selected from a dehiscent wound, a delayed or incompletely healing wound, a chronic wound, a vasculitic ulcer, a venous ulcer or a venous stasis ulcer, an arterial ulcer, a pressure ulcer or a decubitus ulcer, a diabetic ulcer, and a skin ulcer resulting from trauma, or a skin ulcer resulting from a burn.

5. A method according to claim 1 wherein the subject is diabetic.

6. A method according to claim 1 wherein the subject is a human.

7. A method according to claim 1 wherein the subject is a non-human animal, optionally a horse, a dog or a cat.

8. A method according to claim 1, wherein the anticonnexin 43 polynucleotide is administered in an amount ranging from about 1 to about 100 µg per square centimeter of wound size.

9. A method according to claim 8 wherein the administration of said anti-connexin 43 polynucleotide is repeated.

10. A method according to claim 8 wherein the administration of said anti-connexin 43 polynucleotide is repeated about once per week, whereby wound healing is promoted.

11. A method of treating a subject having a delayed healing, incompletely healing, or chronic wound which comprises administration to the wound of an article of manufacture comprising a connexin 43 antisense polynucleotide present at a concentration from 1.0 to about 40.0 milligrams per milliliter whereby connexin 43 expression is downregulated over a sustained period of time.

12. A method according to claim 11 wherein connexin 43 expression is downregulated for at least about 0.5 hours, at least about 1-2 hours, at least about 2-4 hours, at least about 4-6 hours, or at least about 6-8 hours.

13. A method of promoting wound healing in a subject having a delayed healing or chronic wound which comprises administration of an article of manufacture comprising a therapeutically effective amount of a connexin 43 antisense polynucleotide present at a concentration from 1.0 to about 40.0 milligrams per milliliter to a wound area effective to increase re-epithelialization rates in the wound area.

14. A method according to claim 13 wherein the antisense polynucleotide is administered in a sustained release formulation.

15. A method according to claim 13 wherein the polynucleotide is administered for a sustained period of time.

16. A method according to claim 13 wherein the antisense polynucleotide is effective to decrease connexin 43 levels for at least about 0.5 hours, at least about 1-2 hours, at least about 2-4 hours, at least about 4-6 hours, or at least about 6-8 hours.

17. A method of promoting re-epithelialization of wounds which comprises administering to a subject having a delayed healing, incomplete healing or chronic wound a composition comprising a hydrogel and an anticonnexin 43 polynucleotide in an amount effective to promote re-epithelialization.

18. A method according to claim 17 wherein the anticonnexin 43 polynucleotide is an connexin 43 antisense polynucleotide.

19. The method of any one of claim 1, 11, or 17, further comprising administration of a pharmaceutical composition comprising a connexin 31.1 antisense polynucleotide.

20. A method according to any of claim 1, 11 or 17 wherein the antisense polynucleotide comprises a sequence selected from SEQ.ID.NOS.:1 or 2.

21. A method according to any of claim 1, 11 or 17 wherein the antisense polynucleotide has at least about 70 percent homology with SEQ.ID.NOS.:1 or 2.

22. A method according to any of claim 1, 11 or 17 wherein the connexin 43 antisense polynucleotide hybridizes to connexin 43 mRNA under conditions of medium to high stringency.

* * * * *